United States Patent
Borole et al.

(10) Patent No.: US 10,760,169 B2
(45) Date of Patent: Sep. 1, 2020

(54) BIOELECTROCHEMICAL BIOREFINING FOR THE CONVERSION OF HYDROGENOUS MATTER TO HYDROGEN GAS AND OTHER USEFUL PRODUCTS

(71) Applicant: UT-Battelle, LLC, Oak Ridge, TN (US)

(72) Inventors: Abhijeet P. Borole, Knoxville, TN (US); Alex James Lewis, Knoxville, TN (US)

(73) Assignees: UT-Battelle, LLC, Oak Ridge, TN (US); University of Tennessee Research Foundation, Knoxville, TN (US)

(*) Notice: Subject to any disclaimer, the term of this patent is extended or adjusted under 35 U.S.C. 154(b) by 303 days.

(21) Appl. No.: 15/623,794

(22) Filed: Jun. 15, 2017

(65) Prior Publication Data
US 2017/0362719 A1    Dec. 21, 2017

Related U.S. Application Data

(60) Provisional application No. 62/351,322, filed on Jun. 17, 2016.

(51) Int. Cl.
C25B 3/00        (2006.01)
C25B 3/02        (2006.01)
(Continued)

(52) U.S. Cl.
CPC ............... *C25B 3/04* (2013.01); *C12M 35/02* (2013.01); *C12N 13/00* (2013.01); *C12P 3/00* (2013.01);
(Continued)

(58) Field of Classification Search
CPC ................ C25B 3/00; C25B 3/02; C25B 3/04
(Continued)

(56) References Cited

U.S. PATENT DOCUMENTS 7,695,834 B1 * 4/2010  Borole ............... H01M 4/8605
                                                                427/115
8,192,854 B2   6/2012  Borole
(Continued)

OTHER PUBLICATIONS

Kadier et al., "A Comprehensive Review of Microbial Electrolysis Cells (MEC) Reactor Designs and Configuration for Sustainable Hydrogen Gas Production," Alexandria Engineering Journal (2016), vol. 55, pp. 427-443. (Year: 2016).*
(Continued)

*Primary Examiner* — Edna Wong
(74) *Attorney, Agent, or Firm* — Scully, Scott, Murphy & Presser, P.C.

(57) ABSTRACT

A method for the substantially complete conversion of hydrogenous matter to higher value product, the method comprising: (i) subjecting the hydrogenous matter to a substantially complete deconstruction process in which an aqueous phase containing a multiplicity of deconstructed compounds is produced; and (ii) contacting the aqueous phase with an anode of a microbial electrolysis cell, the anode containing a community of microbes thereon which oxidatively degrade one or more of the oxygenated organic compounds in the aqueous phase to produce protons and free electrons at the anode, wherein the protons and free electrons are transported to the cathode to produce hydrogen gas or a valuable reduced organic compound at the cathode upon application of a suitable cell potential across the anode and cathode. The invention is also directed to an apparatus for practicing the method described above.

24 Claims, 12 Drawing Sheets

(51) Int. Cl.

| | |
|---|---|
| C25B 3/04 | (2006.01) |
| C12P 7/06 | (2006.01) |
| C12P 7/16 | (2006.01) |
| C12P 7/18 | (2006.01) |
| C12M 1/42 | (2006.01) |
| C12P 3/00 | (2006.01) |
| C12N 13/00 | (2006.01) |

(52) U.S. Cl.
CPC .............. *C12P 7/065* (2013.01); *C12P 7/16* (2013.01); *C12P 7/18* (2013.01); *Y02E 50/10* (2013.01); *Y02E 50/17* (2013.01)

(58) Field of Classification Search
USPC ............................... 205/413, 450, 452, 462
See application file for complete search history.

(56) References Cited

U.S. PATENT DOCUMENTS

| 8,597,513 B2 | 12/2013 | Borole et al. |
| 8,962,165 B2 | 2/2015 | Logan |

OTHER PUBLICATIONS

Lewis et al., "Hydrogen Production from Switchgrass via an Integrated Pyrolysis-Microbial Electrolysis Process, "Bioresource Technology (2015), vol. 195, pp. 231-241. (Year: 2015).*
Shen et al., "Microbial Electrolysis Cell to Treat Hydrothermal Liquefied Wastewater from Cornstalk and Recover Hydrogen: Degradation of Organic Compounds and Characterization of Microbial Community," International Journal of Hydrogen Energy (2016), vol. 41, pp. 4132-4142. (Year: 2016).*
Kadier et al., "Recent Advances and Emerging Challenges in Microbial Electrolysis Cells (MECs) for Microbial Production of Hydrogen and Value-Added Chemicals," Renewable and Sustainable Energy Reviews (2016), vol. 16, pp. 501-525. (Year: 2016).*
Thygesen et al., "Integration of Microbial Electrolysis Cells (MECs) in the Biorefinery for Production of Ethanol, H2 and Phenolics," Waste Biomass Valor (2010), vol. 1, pp. 9-20. (Year: 2010).*
Guo et al., "Engineering Electrodes for Microbial Electrocatalysis," Current Opinion in Biotechnology (2015), vol. 33, pp. 149-156. (Year: 2015).*
Kundu et al., "An Overview of Cathode Material and Catalysts Suitable for Generating Hydrogen in Microbial Electrolysis Cell," International Journal of Hydrogen Energy (2013), vol. 38, pp. 1745-1757. (Year: 2013).*
Kadier et al., "Recent Advances and Emerging Challenges in Microbial Electrolysis Cells (MECs) for Microbial Production of Hydrogen and Value-Added Chemicals," Renewable and Sustainable Energy Reviews (2016), vol. 61, pp. 501-525. (Year: 2016).*
Pant et al., "Integrated Conversion of Food Waste Diluted with Sewage into Volatile Fatty Acids Through Fermentation and Electricity Through a Fuel Cell," Environmental Technology (2013), vol. 34, Nos. 13-14, pp. 1935-1945. (Year: 2013).*
Ren et al., "Bioconversion of Lignocellulosic Biomass to Hydrogen: Potential and Challenges," Biotechnology Advances (2009), vol. 27, pp. 1051-1060. (Year: 2009).*
Borole, A.P. et al., "Improving energy efficiencyand enabling water recycling in biorefineries using bioelectrochemical systems", Biofuels, Bioprod. Bioref. 5:28-36 (2011).
Borole. A.P. et al., "Conversion of Residual Organics in Corn Stover-Derived Biorefinery Stream to Bioenergy via a Microbial Fuel Cell", Environ. Sci. Technol. 2013, 47, 642-648.
King, D. et al., "II.A.1 Biomass-Derived Liquids Distributed (Aqueous Phase) Reforming", DOE Hydrogen and Fuel Cells Program, FY 2012 Annual Progress Report, 4 pages.
Lewis, A.J. et al., "Understanding the impact of flow rate and recycle on the conversion of a complex biorefinery stream using a flow-through microbial electrolysis cell", Biochemical Engineering Journal 116 (2016) 95-104.
Lewis, A.J. et al., "Hydrogen production from switchgrass via an integrated pyrolysis-microbial electrolysis process", Bioresource Technology 195 (2015) 231-241.
Ortiz-Toral, P.J., "Steam reforming of water-soluble fast pyrolysis biooil: Studies on bio-oil composition effect, carbon deposition, and catalyst modifications", (2011). Graduate Theses and Dissertations. Paper 11965., 144 pages.
Jones, S. et al., "Process Design and Economics for the Conversion of Lignocellulosic Biomass to Hydrocarbon Fuels: Fast Pyrolysis and Hydrotreating Bio-oil Pathway", PNNL, (Nov. 2013), 97 pages.
Sharma, A. et al., "Biomass pyrolysis—A reviewofmodelling,processparameters and catalyticstudies", Renewable and Sustainable Energy Reviews 50 (2015)1 081-1096.
Spath, P.L. et al., "Life Cycle Assessment of Hydrogen Production via Natural Gas Steam Reforming", Technical Report, NREL/TP-570-27637, Nov. 2000, (Revised Feb. 2001), 33 pages.
Kan, T. et al., "Lignocellulosic biomasspyrolysis:Areviewofproductproperties and effectsofpyrolysisparameters", RenewableandSustainableEnergyReviews57(2016)1126-1140.

* cited by examiner

BIOELECTROCHEMICAL BIOREFINING FOR THE CONVERSION OF HYDROGENOUS MATTER TO HYDROGEN GAS AND OTHER USEFUL PRODUCTS

CROSS REFERENCE TO RELATED APPLICATION

The present application claims benefit of U.S. Application No. 62/351,322, filed on Jun. 17, 2016, all of the contents of which are incorporated herein by reference.

STATEMENT REGARDING FEDERALLY SPONSORED RESEARCH

This invention was made with government support under Contract Number DE-AC05-00OR22725 between the United States Department of Energy and UT-Battelle, LLC. The U.S. government has certain rights in this invention.

FIELD OF THE INVENTION

The present invention relates to the field of microbial fuel cells and microbial electrolysis cells and their use in the conversion of biomass or waste effluent for the production of energy or useful products. The present invention is also directed to the production of hydrogen gas and other useful products from biomass and waste effluent.

BACKGROUND OF THE INVENTION

The renewable production of commodity chemicals is greatly needed at this time in view of increasing pollution in many parts of the world as a result of a substantial dependency on the combustion of fossil fuels for most energy demands. Renewable hydrogen production, in particular, is a significant need of the future, since hydrogen can enable modern society to meet its transportation needs and minimize extensive use of fossil fuels, thereby positively impacting climate change. Hydrogen is essential for production of drop-in fuels from biomass via the pyrolysis route (Jones, S., et al., Production of gasoline and diesel from biomass via fast pyrolysis, hydrotreating and hydrocracking: A design case. 2009, Pacific Northwest National Laboratory). Hydrogen is required to deoxygenate the biomass to generate high heating value fuels. It can also be used as a stand-alone fuel for vehicles employing fuel cells.

Reforming of fossil fuels, such as natural gas, is currently the most used method for providing hydrogen for bio-fuel production at the present time. Conversion of the bio-oil generated during the pyrolysis process requires significant amounts of natural gas to convert it to fuels equivalent to gasoline and diesel. In turn, the use of natural gas results in an increase in life cycle greenhouse gas emissions (Spath, P. L. and M. K. Mann, Life Cycle Assessment of Hydrogen Production via Natural Gas Steam Reforming. 2001, NREL: Golden, Colo.).

A significant component of the product bio-oil is made up of oxygenated compounds, such as acetic acid, propionic acid, levoglucosan, hydroxyacetone, and furfural, many of which are water-soluble (e.g., Ortiz-Toral, P. J., Steam Reforming of water-soluble fast pyrolysis bio-oil: Studies on bio-oil composition effect, carbon deposition and catalyst modifications, *Biological Engineering* 2011, Iowa State University: Ames, Iowa). The carboxylic acids render the bio-oil a pH of 3 or lower, making it corrosive. Other oxygenates include polar molecules, which induce phase separation over time and make the bio-oil unstable. Thus, there would be a particular benefit in a process that could generate hydrogen gas and other useful products from such polar oxygenates that are otherwise generally of low value.

SUMMARY OF THE INVENTION

In one aspect, the instant disclosure is directed to a method for converting hydrogen-containing (i.e., hydrogenous) matter of generally little or no value into one or more higher value products, such as hydrogen gas or one or more commodity chemicals, such as alcohols or organic diols. The invention described herein achieves this by substantially completely breaking down (i.e., substantially completely deconstructing) hydrogenous matter and conveying the deconstructed matter, at least a portion of which is in the form of an aqueous phase rich in oxygenated organic compounds soluble in water, to a microbial electrolysis cell (MEC) where the deconstructed matter in the aqueous phase is converted by the MEC to one or more useful products. In some embodiments, the deconstruction process also produces an organic phase rich in hydrocarbons that is substantially insoluble in water, such as provided in a pyrolysis process, and the organic phase is also converted to higher value product. In such a case, the aqueous phase and organic phase are separated before the aqueous phase is conveyed to the MEC. The method results in the substantially complete conversion of hydrogenous matter to higher value product.

More specifically, the method includes: (i) subjecting hydrogenous matter to a substantially complete deconstruction process in which a multiplicity of deconstructed compounds are produced, wherein at least a portion of the deconstructed compounds are oxygenated organic compounds substantially dissolved within an aqueous phase; and (ii) contacting the aqueous phase with an anode of a microbial electrolysis cell, the anode containing a community of microbes thereon which oxidatively degrade one or more of the oxygenated organic compounds in the aqueous phase to produce protons and free electrons at the anode, wherein the protons migrate from the anode across an ion-permeable partition to a cathode also in the microbial electrolysis cell, wherein the ion-permeable partition separates the anode from the cathode; and the free electrons are transported from the anode to the cathode by an electrically conductive wire connecting the anode with the cathode, and the cell potential of the microbial electrolysis cell is adjusted by application of an external voltage between the anode and the cathode to result in production of the higher value product at the cathode. In some embodiments, such as in a pyrolysis process, the aqueous phase is separated from an organic phase also produced in the deconstruction process, and the organic phase is also converted to one or more higher value products. In this way, the process described herein results in the conversion of a substantial portion or nearly all (e.g., at least 75, 80, 85, or 90%) of the hydrogenous matter into higher value product, which represents the sum total of all higher value products produced in the overall conversion of hydrogenous matter (including and beyond the products from the MEC process), whether the higher value products are present in an aqueous-based form, organic-based (hydrophobic or oil-based) form, or gaseous form, or combination thereof.

In some embodiments, the higher value product being produced at the cathode is hydrogen gas, while in other embodiments, the higher value product being produced at the cathode is a commodity chemical, such as an alcohol or diol, e.g., ethanol, butanol, propanediol, or butanediol. In some embodiments, hydrogen gas is produced along with one or more commodity chemicals. Generally, to produce a commodity chemical, the cathode contains on its surface a community of electrotrophic microbes capable of protonation-reduction of at least one of the oxygenated organic compounds at the cathode. The cathode should also be operated in a substantially oxygen-free environment.

In another aspect, the instant disclosure is directed to an apparatus for achieving the above-described method for converting hydrogenous matter to higher value product. More particularly, the apparatus includes a compartment in which at least one heating element is housed to deconstruct hydrogenous matter and produce an aqueous phase rich in oxygenated organic compounds soluble in water from the deconstructed hydrogenous matter; a microbial electrolysis cell containing an anode, a cathode, an ion-permeable partition separating the anode from the cathode, and an electrical power source that regulates a voltage between the anode and cathode, wherein the anode contains a community of microbes thereon which oxidatively degrade one or more of the oxygenated organic compounds in the aqueous phase to produce protons and free electrons at the anode; and a conduit for transporting the aqueous phase from the compartment to the anode of the microbial electrolysis cell.

BRIEF DESCRIPTION OF THE FIGURES

FIG. 2A: Graph showing percent yield of hydrogen gas from a bio-oil aqueous phase under batch conditions at a loading of 0.1 to 0.3 g/L for the PME process for producing hydrogen from switchgrass biomass. FIG. 2B: Graph showing the percent yield of hydrogen gas from a bio-oil aqueous phase for a continuous operation at a loading rate from 2 to 10 g/L-day.

FIG. 3A: Graph showing productivity of hydrogen gas from bio-oil aqueous phase in liters of $H_2$ per liter of anode volume per day for the PME process under batch conditions for producing hydrogen from switchgrass biomass. FIG. 3B: Graph showing hydrogen productivity during continuous operation at a loading rate from 2 to 10 g/L-day.

FIG. 4A: Graph showing anode coulombic efficiency of hydrogen production from bio-oil aqueous phase under batch conditions at a loading of 0.1 to 0.3 g/L for the PME process for producing hydrogen from switchgrass biomass. FIG. 4B: Graph showing anode coulombic efficiency during continuous operation at a loading rate from 2 to 10 g/L-day.

FIG. 5A: Graph showing cathode conversion efficiency of hydrogen production from bio-oil aqueous phase under batch conditions at a loading of 0.1 to 0.3 g/L for the PME process for producing hydrogen from switchgrass biomass. FIG. 5B: Graph showing cathode conversion efficiency during continuous operation at a loading rate from 2 to 10 g/L-day.

FIG. 6A: Graph showing process energy efficiency of hydrogen production from bio-oil aqueous phase under batch conditions at a loading of 0.1 to 0.3 g/L for the PME process for producing hydrogen from switchgrass biomass. FIG. 6B: Graph showing process energy efficiency during continuous operation at a loading rate from 2 to 10 g/L-day.

FIG. 7A: Graph showing electrical energy efficiency of hydrogen production from bio-oil aqueous phase under batch conditions at a loading of 0.1 to 0.3 g/L for the PME process for producing hydrogen from switchgrass biomass. FIG. 7B: Graph showing electrical energy efficiency during continuous operation at a loading rate from 2 to 10 g/L-day.

FIG. 8A: Graph showing removal of major water soluble hydrogenous compounds from switchgrass-derived pyrolysis aqueous phase under batch conditions at a loading of 0.1 to 0.3 g/L for the PME process for producing hydrogen from switchgrass biomass. FIG. 8B: Graph showing removal of major hydrogenous compounds during continuous operation at a loading rate from 2 to 10 g/L-day. The column designated as "total" includes all peaks quantified by high pressure liquid chromatography, which contribute 33% to the chemical oxygen demand of boap (LG—Levuglucosan, AA—Acetic acid, PA—Propionic acid, HMF—Hydroxymethylfurfural, FF—Furfural).

FIGS. 9A and 9B show 16S rRNA microbial characterization of biofilm communities from two anodes from replicate MEC reactors. The presence of families in both samples indicates reproducibility of those members of the community in the anode.

FIG. 10A: Graph showing hydrogen productivity from pine wood-derived catalytic pyrolysis aqueous phase under continuous conditions at a loading of 2 to 50 g/L-day for the MEC for producing hydrogen from pine wood saw dust. FIG. 10B: Graph showing hydrogen yield from the same process at various organic loading rates.

DETAILED DESCRIPTION OF THE INVENTION

Figure 1:
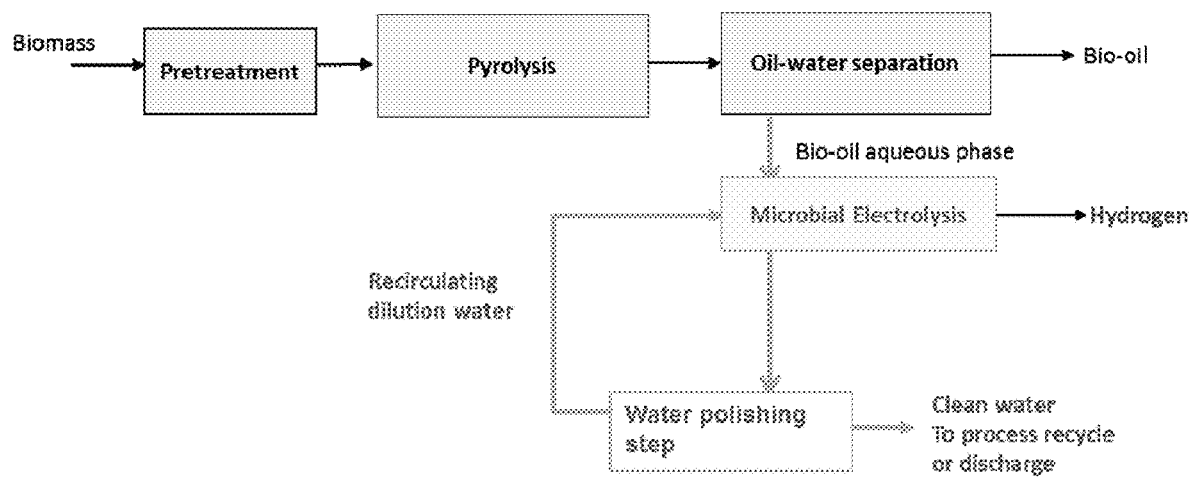
FIG. 1. Flow diagram showing an exemplary integrated pyrolysis-microbial electrolysis (PME) process for hydrogen production from biomass.

In one aspect, the invention is directed to a method for the substantially complete conversion of hydrogenous matter to higher value products, such as hydrogen gas, a hydrocarbon fuel, or commodity chemical (e.g., alcohol or diol). The term "hydrogenous matter," as used herein, refers to hydrogen-containing organic (carbonaceous) matter, wherein the bulk or substantial portion of the hydrogen is generally in atomic form and bound to carbon atoms, i.e., in the form of C—H bonds. Typically, as in most carbonaceous matter, some of the hydrogen atoms are generally also present on one or more heteroatoms, e.g., in the form of O—H, N—H, or S—H bonds. The hydrogenous matter considered herein is generally of little or no value in the sense that it cannot be directly used as a useful material, such as a fuel or commodity chemical, and is generally regarded as waste. Some examples of hydrogenous matter include biomass, municipal waste, food waste, and organic industrial waste (e.g., fracking or petroleum processing waste). The term "substantially complete conversion" generally corresponds to at least or more than 75%, 80%, 85%, or 90% by weight of the hydrogenous matter being converted to higher value product. As indicated above, the foregoing percentages represent the sum total of all higher value products produced in the overall conversion of hydrogenous matter (including and beyond the products from the MEC process), whether the higher value products are present in an aqueous-based form, organic-based (hydrophobic or oil-based) form, or gaseous form, or a combination thereof. Thus, for example, starting with 100 g of biomass in the described process, at least 75 g, 80 g, 85 g, or 90 g of the biomass will generally be converted into higher value product (with no more than 25 g, 20 g, 15 g, or 10 g of the biomass, respectively, not being converted to higher value product). In some embodiments, the conversion process may be conducted as a continuous process in which the aqueous phase is continuously fed to the anode of the MEC. In other embodiments, the conversion process may be conducted as a batch process in which separate batches of aqueous phase of same or different composition are fed to the anode of the MEC at intervals.

In particular embodiments, the hydrogenous matter is biomass. The biomass is generally any form of cellulosic, lignin, or lignocellulosic matter. Some examples of biomass include grasses (e.g., switchgrass, miscanthus, wheat straw, rice straw, barley straw, alfalfa, bamboo, hemp), cornstover (e.g., the leaves, husks, stalks, or cobs of corn plants), sugarcane, bagasse, hull or shell material (e.g., peanut, rice, and walnut hulls), wood (e.g., hardwood or softwood), saw dust, paper or wood pulp, agricultural waste, and forest waste.

The process first involves subjecting the hydrogenous matter to a substantially complete deconstruction process in which a multiplicity of deconstructed compounds are produced. The term "substantially complete deconstruction" generally corresponds to at least or above 75%, 80%, 85%, or 90% by weight of the hydrogenous matter being deconstructed into a multiplicity of deconstructed compounds, at least a portion of which is incorporated into an aqueous phase. The deconstructed compounds are the compounds produced from the deconstruction process. For purposes of the invention, a substantial portion of the deconstructed compounds are organic compounds having C—H bonds that do not escape as gases during the deconstruction process or form solids such as biochar during the deconstruction process, and at least a portion of the deconstructed compounds are oxygenated organic compounds substantially dissolved within an aqueous phase. The term "substantially dissolved," as used herein, generally refers to at least or more than 50, 55, 60, 65, 70, 75, 80, 85, 90, or 95 wt % of oxygenated organic compounds within the aqueous phase being dissolved in the aqueous, while the remaining amount of oxygenated organic compounds may be within the aqueous phase in colloidal or suspension form. In some embodiments, the oxygenated organic compounds are completely dissolved in the aqueous phase with no colloid or suspension. Notably, many of the oxygenated organic compounds present in the bio-oil are substantially amphiphilic, and thus, are able to partition to nearly equal extent in water and organic phases. For this reason, with an initial amount of water, the total dissolved amount of oxygenated organic compounds in the aqueous phase may be fairly low, e.g., about 50% or 60%. However, if additional water is added, then many of these amphiphilic compounds will become further dissolved in the aqueous phase, e.g., at least 70, 80, 90, or 100 wt % of the oxygenated organic compounds may become completely dissolved in the aqueous phase.

The term "aqueous phase" indicates the presence of water. In some embodiments, the aqueous phase includes the oxygenated organic compounds substantially dissolved in water. In other embodiments, the aqueous phase includes the oxygenated organic compounds substantially dissolved in a mixture of water and a water-miscible organic solvent, such as an alcohol. In the case of a mixture of water and a water-miscible organic solvent, the water is generally present in an amount of at least 30, 40, 50, 60, 70, 80, or 90% by volume of the mixture of solvents. The oxygenated organic compounds can be any compounds composed of at least carbon, hydrogen, and oxygen atoms. Some examples of such compounds include organic acids (e.g., formic, acetic, propanoic, and butanoic acids), alcohols (e.g., methanol, ethanol, n-propanol, isopropanol, n-butanol, isobutanol, sec-butanol, and t-butanol), phenol, furan, aldehydes (e.g., furfural), sugars, ketone compounds (e.g., hydroxyacetone), levoglucosan, and their oligomers.

The deconstruction process can be any process capable of substantially breaking down organic hydrogenous matter into a multiplicity of deconstructed compounds that are also hydrogenous, with at least a portion of the deconstructed compounds being oxygenated organic compounds, and with the oxygenated organic compounds being substantially dissolved in an aqueous phase. In some embodiments, the deconstruction process relies on at least thermal means (e.g., pyrolysis) for deconstructing the hydrogenous matter. In other embodiments, the deconstruction process relies on at least chemical means (e.g., acid or alkali hydrolysis, or ammonia explosion) for deconstructing the hydrogenous matter. Some examples of deconstruction processes include pyrolysis, hydrolysis, gasification, hydrothermal liquefaction, and a hydromechanical breakdown. All of the foregoing processes are well known in the art.

The aqueous phase produced in the deconstruction process functions as a substrate for the microbial electrolysis cell (MEC) in order for the MEC to convert the deconstructed oxygenated organic compounds to higher value product. In some embodiments, the deconstruction process results in substantially or completely all of the deconstructed compounds being oxygenated organic compounds dissolved within an aqueous phase, which is then processed by the MEC. In other embodiments, the deconstruction process results in some of the deconstructed compounds being oxygenated organic compounds dissolved within an aqueous phase and some of the deconstructed compounds being hydrophobic compounds (e.g., hydrocarbon compounds) substantially insoluble in an aqueous phase and substantially dissolved in a liquid organic phase. In the latter case, the oxygenated organic compounds are converted by the MEC to higher value product, and the hydrophobic compounds in the liquid organic phase are further processed by means other than the MEC, if necessary, to convert them to higher value product. In this way, whether from a sole aqueous phase or from an aqueous phase in tandem with an organic phase, a substantial portion of the hydrogenous matter by weight is converted to higher value product.

If a liquid organic phase is also produced, the liquid organic phase should be separated from the aqueous phase before the aqueous phase is contacted with the anode of the MEC. In some embodiments, separation of the two phases is achieved by cooling a two-phase system to a sufficiently low temperature (e.g., at or below 20, 15, 10, or 5° C.) at which separation occurs. The cooling process may include vigorous mixing followed by standing at the reduced temperature. The cooling process may also include mixing the two-phase system with additional water or additional organic solvent before or during cooling and vigorous mixing. In other embodiments, the two-phase system is centrifuged with or without cooling and/or vigorous mixing and/or addition of water or organic solvent to effect separation.

The microbial electrolysis cell (MEC) can have the same construction as a microbial fuel cell (MFC), but the MEC is operated under different conditions than an MFC. In an MFC, microbial breakdown of organic compounds into protons and electrons and carbon dioxide occurs at an anode containing a community of microbes having such capability, and the protons and electrons migrate to the cathode where they combine with oxygen to produce water and electrical power. In an MEC, microbial breakdown of organic compounds also occurs at an anode containing a community of microbes having such capability, and the protons and electrons also migrate to the cathode. However, in an MEC, the region surrounding the cathode is deoxygenated; thus, the protons and electrons at the cathode cannot produce water and electricity. In an MEC, the protons and electrons at the cathode instead react by reductively protonating chemical species in contact with the cathode. If the protons at the cathode are the only species present that are capable of being reduced, then hydrogen gas is produced at the cathode. If a reducible organic species is also present at the cathode, then reduced organic species and possibly also hydrogen gas are produced at the cathode. Another difference between an MFC and an MEC is that an MEC requires the application of an external voltage between the anode and the cathode to result in production of hydrogen gas and/or reduced organic species at the cathode, while an MFC produces electricity from the breakdown of organic species.

The MEC contains an anode, a cathode, an electrically conductive wire connecting the anode with the cathode, an ion-permeable partition separating the anode from the cathode, and an electrical power source that regulates a voltage between the anode and cathode. The anode contains a community of microbes thereon which oxidatively degrade one or more of the oxygenated organic compounds in the aqueous phase to produce protons and free electrons at the anode. The MEC also typically includes an anode compartment which contains the anode and an anolyte solution in contact with the anode; and a cathode compartment which contains the cathode and a catholyte solution in contact with the cathode. In operation, the anolyte can be or can include the aqueous phase derived from the deconstruction process, as described above; and the catholyte can be or can include an aqueous phase containing an electrolyte suitable for production of hydrogen gas or reduced organic product (i.e., reduced organic compounds) at the cathode.

The anode can be constructed of any electrically conductive material known in the art suitable for the purposes described herein. The anode material is preferably amenable to the growth and adherence of microbes. Some classes of electrode materials or a coating thereof include conductive metals (e.g., silver, gold, titanium, nickel, cobalt, tungsten, molybdenum, stainless steel, and alloys thereof), conductive polymers, or a metal-deposited carbon anode (e.g., Fe-deposited carbon anode). Particularly preferred for the anode are electrodes based on conductive (elemental) carbon. Typically, any structural form of carbon is suitable as a conductive carbon material. Some examples of carbon electrodes include carbon fiber, carbon paper, carbon foam (e.g., reticulated vitreous carbon), carbon cloth, carbon felt, carbon wool, carbon granules, carbon brushes, graphite, or a combination thereof. The conductive carbon material can have any suitable physical characteristics, such as having a porous, non-porous, powderized, grainy, fibrous, brush, nanotextured, or patterned texture. The conductive carbon material can also be of a less typical form of carbon, such as carbon nanotubes (e.g., single or double walled) or fullerenes. The anode can also have any of the three-dimensional architectures known in the art that are known to possess high porosity values and high flow-through rates. Alternatively, the anode can have a flat (e.g., planar or two-dimensional) topology.

The anode is preferably porous, and in particular, by having a porosity value of at least about 0.3 (and more preferably at least about 0.4, 0.5, 0.6, 0.7, 0.8, or 0.9), wherein the porosity value recited herein is calculated as the volume of void space over the total (i.e., bulk) volume. The foregoing porosity values can be recited as percentages (e.g., 0.3 corresponds to 30%). The anode also preferably possesses sufficient hydraulic conductivity such that the effluent can be processed in a manner that is commercially viable and efficient. For example, it is preferable for the anode to have a hydraulic conductivity of at least 0.5 cm/s, or 1.0 cm/s, or 5.0 cm/s, or 10 cm/s, or 20 cm/s, or 30 cm/s, or 40 cm/s, or 50 cm/s, or 60 cm/s, or 70 cm/s, or 80 cm/s, 90 cm/s, or 100 cm/s, or 110 cm/s, or 120 cm/s.

The anode can also have any suitable shape. The shape of the anode can be, for example, planar (e.g., 50 cm×50 cm×5 cm), block-shaped, columnar, spherical (e.g., 4 cm to 40 cm diameter), ovoid, cuboidal (e.g., 1 cm×1 cm×1 cm or 20 cm×20 cm×20 cm), or mesh. The anode can also be layered or segregated by containing layers or regions of the same or different anode materials.

The ratio of the total volume of the anode (including void volume inside a porous anode) to the volume of the anode chamber (i.e., the "volume ratio") may be, for example, within a range of 0.1 to 0.4. However, as such small volume ratios can be conducive to the growth of non-exoelectrogenic organisms, the use of higher volume ratios (i.e., greater than 0.4) may be used to encourage the growth of exoelectrogenic organisms. For example, in some embodiments, an anode volume ratio of at least 0.5, 0.6, 0.7, 0.8, or 0.9 may be used. In some embodiments, the volume ratio is approximately 1 (i.e., at or greater than 0.95), thereby attaining a dead volume of essentially zero in the anode chamber.

The surface area to volume ratio (specific surface area) for the anode can be any suitable value. As understood in the art, the anode volume being considered in calculating specific surface area includes the void space of the anode, and not the volume that the mass of the anode material itself occupies. The specific surface area is typically at least 50 $m^2/m^3$, and more preferably, at least 60 $m^2/m^3$, 70 $m^2/m^3$, 80 $m^2/m^3$, 90 $m^2/m^3$, 100 $m^2/m^3$, 150 $m^2/m^3$, 200 $m^2/m^3$, 250 $m^2/m^3$, 400 $m^2/m^3$, or 500 $m^2/m^3$. Generally, higher specific surface areas (i.e., preferably at least 1,000 $m^2/m^3$) improve the growth of exoelectrogenic organisms and increase power density during operation of the MEC. In different embodiments, the higher specific surface area can be, for example, at least 5,000 $m^2/m^3$, 10,000 $m^2/m^3$, 30,000 $m^2/m^3$, 40,000 $m^2/m^3$, 45,000 $m^2/m^3$, or 50,000 $m^2/m^3$. High specific surface areas are preferably attained by use of a carbon felt or three-dimensional anode. Any ranges of specific surface areas resulting from any of the values set forth above are also contemplated herein.

Particularly in the case where the anode is constructed of a hydrophobic type of material (e.g., a carbon form), the anode can be rendered sufficiently hydrophilic to permit favorable interaction (i.e., adherence, interfacing, or bonding) of the anode material with aqueous media. The hydrophilicity can also serve to reduce or prevent agglomeration or sticking of hydrophobic compounds or materials (e.g., hydrocarbons and carbonaceous compounds) to the anode. Any method for coating the surfaces of the anode to render them sufficiently hydrophilic is applicable herein. For example, the anode surface can be powder-coated, spraycoated, or dip-coated with one or more hydrophilic polymeric or molecular materials, and optionally thermally processed, calcined, or dried. The anode can also be chemically treated by an oxidizing agent, such as ozone or hydrogen peroxide. The anode can also be treated by ionizing radiation or an ion beam process for this purpose. In a preferred embodiment, the anode is treated by a plasma process to render its surface hydrophilic. The plasma process is preferably an oxygen plasma process.

In one embodiment, the microbes (or a portion thereof) interacting with the anode are planktonic, i.e., flotational. However, planktonic microbes are susceptible to being lost into flowing effluent waters, particularly when the effluent is moving at a high flow rate. To prevent the loss of the microbes into an effluent stream, the planktonic microbes can be contained in a compartment which is permeable to the inflow and outflow of the effluent water and which is non-permeable to the microbes.

In another embodiment, the microbes (or a portion thereof) reside on the anode in the form of a biofilm (i.e., non-planktonic film or mass of microbes). For the purposes of the present invention, a biofilm is preferable since microbes in a biofilm adhere to the anode surface, and are thus significantly less prone to being drawn (and lost) into the flowing effluent. A biofilm of microbes can remain in place with substantially no loss of microbes even at high flow rates.

A biofilm of microbes can be established using any of the methods known in the art. For example, as known in the art, a biofilm of microorganisms can be produced on an anode by initiating a colony of microbes on the anode (i.e., by contact of the anode with the microbes under suitable thriving conditions) and then growing the colony until a biofilm is established on the anode. Preferably, in order to favor growth of exoelectrogenic microbes, the initiation and growth stage is conducted on the anode while the anode is in electrical communication with the cathode. In this way, electrons being donated to the anode from exoelectrogenic microorganisms can be transported to the cathode. The biofilm can be initiated by contact of the anode with an anolyte (i.e., either a specially prepared anodic medium or an aqueous phase from a deconstruction process) that has been inoculated with a sampling of microorganisms, at least a portion of which should be capable of operating by an exoelectrogenic mechanism. Preferably, at some point either at the time of contact, or after contact of the anode with the microorganisms in the anolyte, forced flow and recirculation conditions (i.e., as provided by a pump) are established for the anolyte. For example, in the case of a porous anode, the anolyte is made to flow and recirculate through the anode. A significant portion of microorganisms that do not have a strong propensity for forming biofilms, even though they may be initially associated with the biofilm, will be driven into the anolyte by the flow force. Accordingly, the forced flow and recirculation conditions of the anolyte serve to enrich the biofilm with microorganisms that have a strong propensity for forming biofilms. Further details for producing an adherent and selectively active biofilm of microbes on an electrode are described in detail in, for example, U.S. Pat. No. 8,597,513, the contents of which are herein incorporated by reference in their entirety.

For purposes of the invention, microbes at the anode may be initially enriched by feeding the microbes an aqueous phase simulating an aqueous phase emanating from a deconstruction process. The simulated aqueous phase should contain one or more oxygenated compounds actually found in the aqueous phase emanating from the deconstruction process. The simulated aqueous phase typically includes less than the full variety of compounds that are in an actual aqueous phase emanating from a deconstruction process. The simulated aqueous phase typically also includes a base electrolyte and possibly one or more nutritive substances not found in an actual aqueous phase emanating from a deconstruction process. The microbes at the anode can be fed the simulated aqueous phase for a period of, for example, at least two, three, or four days (or 1, 2, 3 weeks or months) before contacting the anode with an actual aqueous phase emanating from a deconstruction process.

The microorganisms (i.e., organisms) that are used in the anode of the MEC can be any microorganisms capable of oxidatively degrading (i.e., biodegrading) one or more of the oxygenated organic compounds. The microorganism can be, for example, eukaryotic or procaryotic, and either unicellular or multicellular. An example of a suitable unicellular eukaryotic microorganism is yeast. Other examples of unicellular eukaryotic microorganisms include the protists or protozoans, such as amoeba and paramecia. An example of multicellular eukaryotic microorganisms includes the euglena. Those algae capable of uptake of organic carbon (e.g., eukaryotic or procaryotic mixotrophic forms) are also contemplated herein. Procaryotic organisms are predominantly unicellular, and are divided into two domains: the bacteria and the archaea. The procaryotic organisms can also be broadly divided into four main groups according to their shape: the cocci, the bacilli, spirilla, and vibrio. The archaea include the extremophiles (e.g., as found in hot springs and lakes), and the non-extremophiles, as found in soil, the oceans, and marshland. The archaea also include the methanogens.

In one embodiment, the microorganisms considered herein are bacteria. Some examples of phyla of bacteria considered herein are the Acidobacteria, Actinobacteria, Aquificae, Bacteroidetes, Chlorobi, Chlamydiae/Verrucomicrobia, Chloroflexi, Chrysiogenetes, Cyanobacteria, Deferribacteres, Deinococcus-Thermus, Dictyoglomi, Fibrobacteres, Firmicutes, Fusobacteria, Gemmatimonadetes, Nitrospirae, Planctomycetes, Proteobacteria ($\alpha$, $\beta$, $\gamma$, $\delta$ varieties), Spirochaetes, Synergistetes, Tenericutes, Thermodesulfobacteria, Thermotogae, or any combination thereof. Some particularly relevant families of bacteria being considered herein include Acidaminococcaceae, Acidobacteriaceae, Aeromonadaceae, Alteromonadaceae, Clostridiaceae, Comamonadaceae, Desulfobulbaceae, Desulfuromonadaceae, Enterobacteriaceae, Geobacteraceae, Pasturellaceae, Pelobacteraceae, Pseudomonadaceae, Rhodocyclaceae, and Shewanellaceae. Any combination of bacteria containing at least one of the above families of bacteria are also contemplated herein.

In a particular embodiment, the microbes include bacteria from the phylum Firmicutes. Some particular classes of Firmicutes bacteria being considered herein are Bacilli, Clostridia, and Mollicutes. A particular order of Bacilli being considered herein is Lactobacillales, particularly those in the family Enterococcaceae. A particular order of Clostridia being considered herein is Clostridiales. Some particular families of Clostridiales being considered herein are Acidaminococcaceae, Clostridaceae, and Veillonellaceae. Some particular genera of Acidaminococcaea or Veillonellaceae being considered herein are *Acetonema, Acidaminococcus, Allisonella, Anaeroarcus, Anaeroglobus, Anaeromusa, Anaerosinus, Anaerovibrio, Centipeda, Dendrosporobacter, Dialister, Megamonas, Megasphaera, Mitsuokella, Pectinatus, Pelosinus, Phascolarctobacterium, Propionispira, Propionispora, Quinella, Schwartzia, Sele-*

*nomonas, Sporomusa, Sporotalea, Succiniclasticum, Succinispira, Thermosinus, Veillonella*, and *Zymophilus*. Some particular genera of Clostridaceae being considered herein are *Acetanaerobacterium, Acetivibrio, Acidaminobacter, Alkaliphilus, Anaerobacter, Anaerotruncus, Anoxynatronum, Bryantella, Caldanaerocella, Caloramator, Caloranaerobacter, Caminicella, Candidatus Arthromitus, Clostridium, Coprobacillus, Dorea, Ethanologenbacterium, Faecalibacterium, Garciella, Guggenheimella, Hespellia, Linmingia, Natronincola, Oxobacter, Parasporobacterium, Sarcina, Soehngenia, Sporobacter, Subdoligranulum, Tepidibacter, Tepidimicrobium, Thermobrachium, Thermohalobacter*, and *Tindallia*.

In another particular embodiment, the microbes include one or more classes of bacteria from the phlyum Proteobacteria. A particular class of Proteobacteria being considered herein is Alpha Proteobacteria. Some particular orders of Alpha Proteobacteria being considered herein are Caulobacterales (e.g., the family Caulobacteraceae, or *Caulobacter* sp.), Kordiimonadales, Parvularculales, Rhizobiales (e.g., the family Rhizobiaceae, or *Rhizobium* sp.), Rhodobacterales, Rhodospirillales (e.g., the family Acetobacteraceae, or *Acetobacter* sp.), Rickettsiales (e.g., the family Rickettsiaceae, or *Rickettsia* sp.), and Sphingomonadales (e.g., the family Sphingomonadaceae, or *Sphingomonas* sp.), wherein "sp." or "spp." as used herein both indicate one or more species of the indicated genus.

Another particular class of Proteobacteria being considered herein is Beta Proteobacteria. Some particular orders of Beta Proteobacteria being considered herein are Burkholderiales, Hydrogenophilales, Methylophilales, Neisseriales (e.g., the family Neisseriaceae, or *Neisseria* sp.), Nitrosomonadales, Rhodocyclales, and Procabacteriales. A particular family of Burkholderiales being considered herein is Comamonadaceae. Some particular genera of Comamonadaceae being considered herein are *Acidovorax, Aquabacterium, Brachymonas, Comamonas, Curvibacter, Delftia, Hydrogenophaga, Ideonella, Leptothrix, Malikia, Pelomonas, Polaromonas, Rhodoferax, Roseateles, Sphaerotilus, Tepidimonas, Thiomonas*, and *Variovorax*. A particular family of Rhodocyclales being considered herein is Rhodocyclaceae. A particular genus of Rhodocyclaceae being considered herein is *Azospira*.

Another particular class of Proteobacteria being considered herein is Gamma Proteobacteria. Some particular orders of Gamma Proteobacteria being considered herein are Acidithiobacillales, Aeromonadales, Alteromonadales, Cardiobacteriales, Chromatiales (purple sulfur bacteria), Enterobacteriales (e.g., the family Enterobacteriaceae, such as the genera *Escherichia* or *Salmonella*), Legionellales (e.g., the family Legionellaceae, or *Legionella* sp.), Methylococcales, Oceanospirillales, Pasteurellales (e.g., the family Pasteurellaceae, or *Haemophilus* sp.), Pseudomonadales, Thiotrichales (e.g., Thiomargarita), Vibrionales (e.g., the family Vibrionaceae, or *Vibrio* sp.), Xanthomonadales (e.g., the family Xanthomonadaceae, or *Xanthomonas* sp.). A particular family of Aeromonadales being considered herein is Pseudomonadaceae. A particular genus of Pseudomonadaceae being considered herein is *Pseudomonas* (e.g., *P. aeruginosa*). Some particular families of Alteromonadales being considered herein are Shewanellaceae and Pseudoalteromonas. A particular genus of Shewanellaceae being considered herein is *Shewanella* (e.g., *S. putrefaciens*).

Another particular class of Proteobacteria being considered herein is Delta Proteobacteria. Some particular orders of Delta Proteobacteria being considered herein are Aeromonadales, Bdellovibrionales (e.g., the family Bdellovibrionaceae, or *Bdellovibrio* sp.), Desulfobacterales, Desulfovibrionales, Desulfurellales, Desulfarcales, Desulfuromonadales, Myxococcales (Myxobacteria), and Syntrophobacterales. A particular family of Aeromonadales being considered herein is Aeromonadaceae. A particular genus of Aeromonadaceae being considered herein is *Aeromonas*. Some particular families of Desulfuromonadales being considered herein are Desulfuromonadaceae, Pelobacteraceae, and Geobacteraceae. A particular genus of Desulfuromonadaceae being considered herein is *Desulfuromonas*. A particular genus of Geobacteraceae being considered herein is *Geobacter* (e.g., *Geobacter sulfurreducens* and *Geobacter metallireducens*). A particular family of Desulfobacterales being considered herein is Desulfobulbaceae. A particular genus of Desulfobulbaceae being considered herein is *Desulfobulbus*.

Another particular class of Proteobacteria being considered herein is Epsilon Proteobacteria. Some particular orders of Epsilon Proteobacteria being considered herein are Campylobacterales (e.g., the family Helicobacteraceae, or *Helicobacter* sp.) and Nautiliales.

In another particular embodiment, the microbes include one or more bacteria from the phlyum Acidobacteria. A particular order of Acidobacteria being considered herein is Acidobacteriales. A particular family of Acidobacteriales being considered herein is Acidobacteriaceae. Some particular genera of Acidobacteriaceae being considered herein are *Acidobacterium, Geothrix, Holophaga*, and *Chloracidobacterium*.

In another particular embodiment, the microbes include one or more thermophilic bacteria from the order Thermotogales. Some particular genera of Thermotogales being considered herein are *Thermotoga, Caldotoga, Fervidobacterium, Geotoga, Marinitoga, Petrotoga, Thermopallium*, and *Thermosipho*. A related family of thermophilic bacteria being considered herein is Thermoanaerobiaceae. Some particular genera of Thermoanaerobiaceae being considered herein are *Thermoanaerobacter* and *Thermoanaerobacterium*. Some particular species of *Thermoanaerobacter* being considered herein are *Thermoanaerobacter thermohydrosulfuricus, Thermoanaerobacter subterraneus, Thermoanaerobacter brockii, Thermoanaerobacter yonseiensis*, and *Thermoanaerobacter tengcongensis*.

In another embodiment, the microorganisms considered herein are archaea. Some examples of phyla of archaea considered herein are the Crenarchaeota, Euryarchaeota, Korarchaeota, and Nanoarchaeota. Several classes of archaea are methanogens, e.g., Methanomicrobia, Methanobacteria, Methanococci, and Methanopyri. Preferably, methanogens are not used in the method due to their propensity for producing methane and their general lack of ability to function as exoelectrogenic organisms. However, methanogens that can function as exoelectrogenic organisms may be used in the method if they are used under conditions that prevent methane production.

The microbes can be selective or non-selective with respect to oxidative degradation of the oxygenated organic compounds. For example, a consortium or species of microbes may be used which is generally non-selective in its ability to oxidatively degrade a wide variety of different oxygenated organic compounds. A consortium or particular species of microbes may also be somewhat selective in processing oxygenated organic compounds in that the microbes may oxidatively degrade one or more types of oxygenated organic compounds more efficiently or effectively than one or more other types of oxygenated organic compounds. Finally, a consortium or species of microbes may be highly selective in processing one or more specific oxygenated organic compounds while being essentially inefficient or ineffective in processing one or more other oxygenated organic compounds.

In one embodiment, a population of microbes on the anode is relatively homogeneous by having a predominant proportion of the microbe population (typically at least 90%, 95%, 97%, 98%, or 99%) within a particular class, order, family, genus, or species of microorganism. In another embodiment, a population of microbes on the anode is relatively heterogeneous (i.e., a consortium of microbes). A relatively homogeneous or heterogeneous sample of microbes can be obtained by any method known in the art, including as a purified culture (i.e., as prepared by cell culturing methods) or from a non-cultured source. Some examples of non-cultured sources from which a population of microbes can be obtained include, for example, a waste stream (e.g., municipal or industrial waste streams), top soil, hot spring, estuary, deep sea vent, underground environment, highly saline environment, or a contaminated environment (e.g., oil- or hydrocarbon-contaminated environment).

The cathode can be constructed of any suitable electrically conductive material, such as any of the materials described above for the anode. The cathode can also have any of the properties (e.g., porosity and hydraulic conductivity values) described above for the anode. When the MEC is directed to producing hydrogen gas (i.e., at the cathode), the cathode is constructed of a material capable of reducing protons (or a material that promotes reduction of protons) to hydrogen gas. The cathode material can be, for example, a hydrogen-producing metal, such as platinum (Pt), palladium (Pd), molybdenum (Mo), nickel (Ni), iron (Fe), copper (Cu), or an alloy thereof (e.g., stainless steel). Other possible hydrogen-producing materials include hydrogen-producing enzymes or microbes. In embodiments where the MEC is directed to reductively converting at least one organic precursor compound to a reduced organic compound (i.e., at the cathode), the cathode preferably includes on its surface a biological system capable of transferring or utilizing electrons. In such a case, the cathode can be termed a "biocathode." More particularly, the cathode can include on its surface a community of electrotrophic microbes (i.e., electrotrophs) capable of protonation-reduction of at least one organic precursor compound at the cathode. As known in the art, an electrotroph has the ability to accept electrons from an electrode and also transfer electrons to an acceptor molecule to provide a reduced version of the acceptor molecule. Electrotrophs are described in detail in, for example, D. R. Lovely, *Environmental Microbiology Reports,* 3(1), pp. 27-35, 2011, the contents of which are herein incorporated by reference in their entirety. In some embodiments, the electrotroph is selected from any of the microorganisms described above for the anode and that possesses electrotrophic behavior. The electrotrophic microbes may also be in the form of a biofilm, as described above for the anode. More particularly, the electrotroph may be, for example, one or more *Geobacter* species.

An anaerobic environment at the cathode is generally required for purposes of the invention. This is typically achieved by deoxygenation of the atmosphere surrounding the cathode. Deoxygenation at the cathode can be conveniently achieved by, for example, sparging of the catholyte with nitrogen (or other inert gas) and/or sealing of the cathodic chamber so as to prevent entry of air.

The spacing between the anode and cathode (i.e., the electrode spacing) can be any suitable spacing. In one embodiment, the spacing is within the range of 0 to 1 cm. Smaller electrode spacings (i.e., less than 1 cm) can also be used. For example, in different embodiments, the electrode spacing can be at about or less than 0.8 cm, or 0.5 cm, or 0.25 cm, or 0.1 cm, or 5 mm, or 4 mm, or 3 mm, or 2 mm, or 1 mm, or 0.5 mm. In another embodiment, the electrode spacing is greater than 1 cm, and can be, for example, at or greater than 2 cm, 5 cm, 10 cm, 20 cm, 30 cm, 40 cm, or 50 cm.

Preferably, in order to maximize output and provide an efficient system, the level of oxygen in the reaction zone of the anode is also reduced, and in some cases substantially reduced, so as to result in an appreciably anaerobic environment at the anode. Any method for removal and exclusion of oxygen at the anode can be used, such as described above for the cathode.

The MEC described herein can have any suitable number of cathodes and anodes. For example, the MEC can be operated with one anode and more than one cathode, or one cathode and more than one anode, or an equivalent number of anodes and cathodes (e.g., two anodes and two cathodes, or three anodes and three cathodes). In addition, the MEC can function monolithically, or alternatively, in a stacked mode in which, for example, 2-250 MEC units are stacked in order to increase product output. Other specifics and modifications known in the art of microbial fuel cell design can be found in, for example, U.S. Pat. No. 8,962,165, which is incorporated herein by reference in its entirety.

The ion-permeable partition separating the anode from the cathode (i.e., separating the anolyte from the catholyte) can be any material that prevents intermixing of anolyte and catholyte solutions, but is ion-permeable so as to at least permit transport of ions from the anolyte to the catholyte. The ion-permeable partition can be of any suitable shape. In some embodiments, the partition is in the shape of a membrane, i.e., a thin sheet or film. In some embodiments, the anolyte and catholyte may be separated by an aqueous permeable membrane such as filter paper, cloth, or a specific molecular-weight cut-off membrane, such as a 30k Dalton cut-off membrane or 0.2 micron membrane.

In some embodiments, the ion-permeable partition is an ion exchange material, or more particularly, a cation-exchange or anion-exchange material, which may be a cation-selective or anion-selective permeable material. In particular embodiments, the ion-permeable partition is a membrane. In the case of a cation-selective partition, the partition selectively allows the diffusion or passage of cations, such as hydrogen ions ($H^+$) to the cathode while not allowing the passage of anions. A particular type of cation-selective permeable material considered herein is a proton-selective permeable material. The cation-selective or proton-selective permeable material can be any such material known in the art having these properties. Typically, the cation- or proton-selective permeable material is in the form of a membrane, otherwise referred to herein as a cation- or proton-selective permeable membrane or cation or proton exchange membrane (PEM). Any of the PEMs known in the art can be used herein, for example, those belonging to the class of ionomer polyelectrolytes having these properties, such as the Nafion® class of PEMs. In some embodiments, the anolyte and catholyte can be separated by a cation- or proton-selective salt bridge, or a glass bridge containing a cation or proton exchange membrane. In the case of an anion-selective partition, the partition selectively allows the diffusion or passage of anions, such as hydroxide (OH) anions, to the anode. This also works, because, in an MEC, the pH at the cathode can be significantly increased (e.g., to a pH of 12 or more) during operation, which results in an elevated concentration of hydroxide ions at the cathode, due to proton consumption. Using an anion exchange membrane allows the hydroxide ions to migrate to the anode. Since the concentration of hydroxide ion at the cathode can be 4-5 orders of magnitude higher than protons at the anode, an anion exchange membrane may be advantageous in some embodiments.

The MEC is typically operated within a mild temperature range of about 20 to 50° C. and normal to elevated pressure conditions (i.e., approximately 1 atm or above). However, if thermophilic or hyperthermophilic organisms are used, the operating temperature of the MEC can be higher (e.g., at about or greater than 50° C., or 60° C., or 70° C., or 80° C., or 90° C., or 100° C.).

After the hydrogenous matter is substantially deconstructed with production of an aqueous phase containing oxygenated organic compounds, the aqueous phase is contacted with an anode of an MEC, as described above, to result in production of the one or more higher value products, such as hydrogen gas and/or a reduced organic product at the cathode. For production of hydrogen gas only, the cathode is maintained in an inert atmosphere and in the substantial absence of organic reducible compounds. In some embodiments, the produced hydrogen gas is directed into a hydrogen-oxygen fuel cell to convert the hydrogen gas to electricity, or the hydrogen gas may be directed into a chemical process in which hydrogen gas is useful, or the hydrogen gas may be recycled into the deconstruction process or a process downstream from the deconstruction process in order to hydrogenate or reduce compounds being produced in the deconstruction process or in a process downstream from the deconstruction process.

The cell potential (voltage, or $\Delta V$) applied between the anode and the cathode is adjusted to result in production of hydrogen gas or a reduced organic compound at the cathode. The cell potential is generally within the range of 0.2 V to −0.45 V vs. the Ag/AgCl reference electrode. In different embodiments, the cell potential applied between the anode and cathode is about, 0.2, 0.1, −0.1, −0.2, −0.3, or −0.4 V, or within a range between any two of the foregoing voltages. In some embodiments, adjusting of the cell potential is achieved by poising the anode without poising the cathode and without maintaining a set potential difference between the anode and cathode. Poising of the anode can be particularly advantageous for maintaining stability of and preventing accidental damage to the biofilm. Nevertheless, in other embodiments, it may be preferable to poise the cathode without poising the anode. In other embodiments, the overall cell potential between the anode and cathode is maintained at a certain voltage or within a certain voltage range, such as any of the voltages provided above, with or without poising the anode or the cathode. In some embodiments, the cell potential is adjusted so that the anode potential (typically around −0.3 V vs. SHE (standard hydrogen electrode potential)) is externally supplemented to make the potential difference between the anode and the cathode at least about 0.41 V. For example, the anode can be externally assisted with a voltage of about 0.11 to 0.25 V or higher for this purpose, depending on the magnitude of the cathode overpotential.

For production of reduced organic compounds, the cathode is maintained in an inert atmosphere and in the presence of one or more organic reducible compounds that function as organic precursor compounds for the production of reduced organic compounds (i.e., reduced organic product) at the cathode. The latter process is also herein referred to as a "bioelectrochemical biorefining process." In some embodiments, the organic precursor compound being contacted with the cathode is a lower value or waste byproduct produced in an industrial process, such as a biomass pretreatment or conversion process. The term "lower value" is relative to the reduced organic compound that the precursor compound can be converted into and as defined above in reference to hydrogenous matter. The organic precursor compound may be, for example, any of the types of oxygenated organic compounds described above, although not necessarily emanating from a deconstruction process. The organic precursor compound can be from any source. The organic precursor compound can be, for example, an organic acid, alcohol, phenol, furan, aldehyde, sugar, ketone compounds, or an oligomer thereof, wherein the organic acid can be a mono-, di-, or tri-acid and the alcohol can be a monohydric, dihydric, trihydric, or tetrahydric alcohol. Some particular examples of organic precursor compounds include acetate, glycerol, succinate, and glucose. In a first exemplary embodiment, the cathode converts an organic acid precursor to an alcohol, e.g., conversion of acetate (which can encompass acetic acid and its salts) to ethanol, or conversion of butyrate to butanol, or conversion of succinate to butanediol. In a second exemplary embodiment, the cathode may convert a dihydric alcohol precursor (i.e., diol) to a monohydric alcohol, or a trihydric alcohol precursor (e.g., glycerol) to a dihydric alcohol (e.g., propanediol). The process may also convert a sugar to an organic acid, e.g., conversion of glucose to lactic acid at the cathode. Depending on such factors as the concentration of reducible organic species at the cathode and the external voltage applied across the anode and cathode, the reduced organic compound may or may not be produced in tandem with production of hydrogen gas.

The cathode of the MEC may also be used for the breakdown or elimination of one or more inorganic chemical species that are typically toxic, environmentally unfriendly, or of low value. Some examples of inorganic chemical species that can be reduced at the cathode include nitrate, perchlorate, and heavy metals (Rabaey, K. et al. *The ISME Journal* 1, 9-18 (2007)).

In one embodiment, the reducible inorganic species is a compound or material containing a nitrogen oxide (N—O) bond. Such a compound is commonly a nitrate-containing species (i.e., "a nitrate" or "nitrate compound"). The nitrate compounds can include inorganic nitrate species (e.g., $NaNO_3$, $KNO_3$, $NH_4NO_3$, $Mg(NO_3)_2$, $AgNO_3$, $HNO_3$, and so on) as well as organonitrate species, such as tetramethylammonium nitrate. Other types of nitrogen oxide compounds that can be reduced include the nitrites, organonitro compounds, dinitrogen tetroxide, nitrosyl (nitroso) compounds, nitric oxide (NO), and nitrosonium species.

In another embodiment, the reducible inorganic species in contact with the cathode is a compound or material containing a halogen oxide bond. A common class of such compounds are the chlorine oxide class of compounds. A common subclass of chlorine oxide compounds are the perchlorates. The perchlorates include inorganic perchlorate species (e.g., $LiClO_4$, $NaClO_4$, $KClO_4$, $NH_4ClO_4$, $Mg(ClO_4)_2$, $AgClO_4$, $HClO_4$, and so on) as well as organoperchlorate species, such as tetramethylammonium perchlorate. Other subclasses of chlorine oxide compounds include the chlorates, chlorites, hypochlorites, and their acids. Other classes of halogen oxide compounds include the bromine oxide and iodine oxide classes of compounds. Some subclasses of bromine oxide compounds include the perbromates, bromates, bromites, hypobromites, and their acids.

Some subclasses of iodine oxide compounds include the periodates, iodates, iodites, hypoiodites, and their acids.

In another embodiment, the reducible inorganic species is a compound (e.g., salt) or material containing one or more reducible metal species. A reducible metal species typically contains a metal atom having a positive oxidation state. The reductive method is particularly effective in reducing heavy metals, which are often harmful to the environment and in need of removal. Some examples of reducible metal species include Cr(VI) as found in chromates and dichromates, Mn(VII) as found in permanganates, Fe(III), Ni(III), Cu(II), Cu(I), Pd(II), Ag(I), Cd(II), Au(III), Au(I), Hg(I), Pb(II), and U(VI), which can be converted to the relatively insoluble U(III) species. The more reducible heavy metals can be reduced to elemental form at the cathode, which can allow for their more facile removal.

In yet another embodiment, the reducible species in contact with the cathode is a peroxide or sulfurous species. The peroxide can be, for example, inorganic (e.g., hydrogen peroxide), or an organoperoxide, such as carbamide peroxide, dibenzoyl peroxide, and cumene hydroperoxide. The sulfurous substance can be, for example, sulfur dioxide, sulfur trioxide, sulfuric acid, a sulfate, a sulfite, a bisulfite, a persulfate (e.g., a peroxodisulfate), or a disulfide.

In one embodiment, an aqueous phase from a deconstruction process is directly fed into an anode of the MEC in order to produce a higher value product at the cathode, as described above. In another embodiment, the aqueous phase is pre-treated before being fed into an anode of the MEC. The pre-treatment step can be any suitable pre-treatment, including, for example, a filtration step, settling step, separation step, pH adjustment step, temperature elevation or reduction step, emulsifying step, precipitation step, or chemical processing step. In some embodiments, an oxidation pre-treatment step (i.e., pre-oxidation treatment step) is employed. An oxidation pre-treatment step can be particularly useful for initiating the oxidation of oxidatively resistant (i.e., recalcitrant) carbonaceous components of the hydrogenous matter, particularly those that are aromatic. The oxidation pre-treatment step can use any oxidant known in the art capable of oxidizing recalcitrant organic compounds to a level sufficient for further processing by the MFC. Preferably, the oxidant is environmentally benign. The oxidant can be, for example, ozone, a peroxide, a halogen-oxide compound, or nitrogen-oxide compound. Alternatively, the oxidation pre-treatment step is a physical process, such as a thermal, electrolytic, or radiative process.

In some embodiments, an oxidative intermediate step is employed on the produced aqueous phase before it reaches the anode of the MEC. In this way, remaining hydrophobic organic compounds that may be difficult or impossible for the microbes to oxidatively degrade can be more easily and more completely degraded. The oxidation process (e.g., ozonation) can advantageously further oxygenate an already oxygenated organic compound, or the oxidation process can oxidize non-oxygenated or low-oxygenated compounds formed in the deconstruction process and that may be present to some degree in the aqueous phase, to render such compounds oxygenated or further oxygenated. In yet another embodiment, an oxidation pre-treatment may be performed on hydrophobic compounds formed in the deconstruction process and not originally present in the aqueous phase, in order to render the hydrophobic compounds oxygenated and capable of incorporation into the aqueous phase.

In particular embodiments, the deconstruction process is a pyrolysis process. The term "pyrolysis," as used herein, and as generally accepted, refers to the thermal decomposition of a material in the substantial absence of oxygen. The pyrolytic process may be, for example, a biomass pyrolysis process, biofuel production process (e.g., biodiesel or bio-oil production process), waste incineration process, or industrial process for the production of a commodity chemical. The temperature employed in the pyrolysis process is generally at least 150° C., and in different embodiments may be at least or above, for example, 200° C., 250° C., 300° C., 350° C., 400° C., 450° C., 500° C., 550° C., 600° C., 650° C., or 700° C., or a temperature within a range bounded by any two of these temperatures.

As well known, biomass can be pyrolyzed to produce any of a variety of biofuels that share a similar chemical profile with a petrochemical blendstock, e.g., gasoline, diesel, or jet fuel. The biomass can be any of the biomass materials known in the art. The biomass can be as exemplified above, such as, for example, wood (e.g., hardwood and softwood), a grass or mixture thereof (e.g., perennial grass or cereal grass), sugarcane (e.g., sugarcane bagasse), paper, cardboard, hull material (e.g., grain hulls or nut hulls, such as corn stover), or a vegetable or algal oil. In the pyrolysis process, biomass is initially converted to a crude pyrolysis oil fraction, which contains a liquid organic phase rich in hydrocarbons substantially insoluble in water (i.e., crude bio-oil) and the aqueous phase rich in oxygenated organic compounds soluble in water (i.e., bio-oil aqueous phase), the latter of which is as described above and which is directed to the anode of the MEC after being separated from the organic phase. Solid biochar and pyrolytic gas is generally also produced. The pyrolysis may be a slow or flash pyrolysis process; however, for purposes of the invention, a flash (or fast) pyrolysis process is generally preferable since this is generally more capable of maximizing the liquid organic phase. Further details of the biomass pyrolysis process are provided in, for example, T. Kan et al., *Renewable and Sustainable Energy Reviews*, vol. 57, pp. 1126-1140, May 2016; A. Sharma et al., *Renewable and Sustainable Energy Reviews*, vol. 50, pp. 1081-1096, October 2015; and U.S. Pat. Nos. 7,998,315 and 8,545,581, the contents of which are herein incorporated by reference in their entirety.

As well known, during pyrolysis, three products are generated: the bio-oil (which includes the aqueous phase containing oxygenated hydrogenous compounds), a non-condensable gas (NCG) phase, and biochar. The yield of biochar is typically about 50-60 wt %. In conversion of bio-oil to higher value product, the biochar and NCG are preferably used to produce either heat or hydrogen. Often, the NCG is added to natural gas to produce additional hydrogen. However, the yield of higher value product from the pyrolysis process has traditionally been low due to the presence of the aqueous phase in the bio-oil. Traditionally, the aqueous phase has been of no use in the pyrolysis process. However, the instant invention solves this problem by directing the aqueous phase to an MEC where the compounds in the aqueous phase are then converted to higher value product. When the amount of higher value product derived from NCG, biochar, and the oil-soluble and aqueous-soluble phases are taken into account, the end result is that a significant portion of the biomass has been converted to higher value product. Thus, by the presently described method, a much more significant portion of the biomass can be converted to higher value product in a pyrolysis process. This significantly increased conversion of biomass to higher value product represents a significant advance in the art of biomass conversion.

The bio-oil aqueous phase from the pyrolysis process is directed to the anode of the MEC, as described above, to break down the oxygenated organic compounds in the aqueous phase and produce hydrogen gas or reduced organic compounds at the cathode. The range of possible organic precursors and reduced organic product are as described above. The crude bio-oil portion of the crude pyrolysis oil may possibly be used as a fuel without further processing; however, most pyrolysis processes include an upgrading step that refines and chemically modifies the initial crude bio-oil to produce a biofuel with a higher quality composition. Typically, after pyrolysis and upgrading steps, the upgraded biofuel stock is fractionated and refined to form the various fuel grades. As both the liquid organic and aqueous phases are substantially or completely deconstructed to crude bio-oil, and the aqueous and liquid organic phases of the crude bio-oil substantially or completely converted to high value products, the pyrolysis-MEC method described herein advantageously results in the substantially complete conversion of hydrogenous matter to higher value product.

In another aspect, the invention is directed to an apparatus for achieving the above-described process for the conversion of hydrogenous matter to higher value end product. The apparatus includes, at minimum, a compartment in which the hydrogenous matter is deconstructed (i.e., "deconstruction chamber") to form an aqueous phase, as described above; an MEC, as described above; and a conduit (e.g., a pipe, tube, or opening in the compartment) for transporting the aqueous phase emanating from the deconstruction process to the anode of the MEC. Typically, the deconstruction chamber includes a heating element for the purpose of heating the hydrogenous matter to a deconstruction temperature, wherein a deconstruction temperature may or may not be used in combination with chemical deconstruction. The heating element is housed within or around the deconstruction chamber, provided that the heating element is capable of raising the temperature within the deconstruction chamber to a deconstruction temperature. In some embodiments, the apparatus also includes an oil-water separation unit for separating the aqueous phase from an organic phase rich. The oil-water separation unit may include, for example, one or more components capable of cooling an oil-water mixture and/or a centrifuging unit. In some embodiments, a pretreatment chamber may also be included, wherein the pretreatment chamber is equipped with the components necessary for pretreating (e.g., oxidative pretreating) of the hydrogenous matter, and also includes a conduit for conveying the pretreated matter to the deconstruction chamber.

Examples have been set forth below for the purpose of illustration and to describe certain specific embodiments of the invention. However, the scope of this invention is not to be in any way limited by the examples set forth herein.

Examples

Pyrolysis-Microbial Electrolysis (PME) Process

An integrated process was employed in which pyrolysis and microbial electrolysis were combined to produce hydrogen from biomass. FIG. 1 is a flow diagram showing the integrated process converting biomass into hydrogen. The microbial electrolysis sub-process includes a method of converting bio-oil aqueous phase generated from pyrolysis of biomass into hydrogen gas, by use of a microbial anode, where the anode comes in contact with the aqueous stream (bio-oil aqueous phase, as-is or diluted with water) and converts the organic compounds in the bio-oil aqueous phase into smaller molecules, electrons, and protons. The anode is in electrical and hydraulic contact with a cathode, where electrons and protons combine to produce hydrogen. In the microbial electrolysis process, the bio-oil aqueous phase is fed into the anode chamber containing an electrogenic consortium of microbes. The consortium is grown using biomass sugars or the organic components present in bio-oil aqueous phase (boap) as the carbon and energy source. The boap compounds are taken up by the anode microorganisms and the electrons produced by them are delivered to the electrode. The protons generated in the process are transferred to the cathode via a membrane present between anode and cathode, where they combine with electrons to produce hydrogen.

Conversion of bio-oil aqueous phase derived from switchgrass to hydrogen was demonstrated using the PME process. The boap is added into a recirculating aqueous stream passing through a porous anode where it is consumed by organisms present in the anode. The boap consists of many classes of compounds, including organic acids, alcohols, aldehydes, esters, ketones, furans, sugars, and phenols. Most of these compounds are converted by the anode organisms into breakdown products used to produce hydrogen. The operation of MEC requires application of a small voltage between anode and cathode. A potential difference of 0.9V was used between the two electrodes. This was done by poising the anode at a potential of −0.2V vs. a Ag/AgCl reference electrode. Operating the MEC by poising the anode offers a unique advantage in terms of the stability of the bioanode operation and prevents accidental damage of the anode microorganisms by exposure to high potentials.

Figures 2A, 2B:
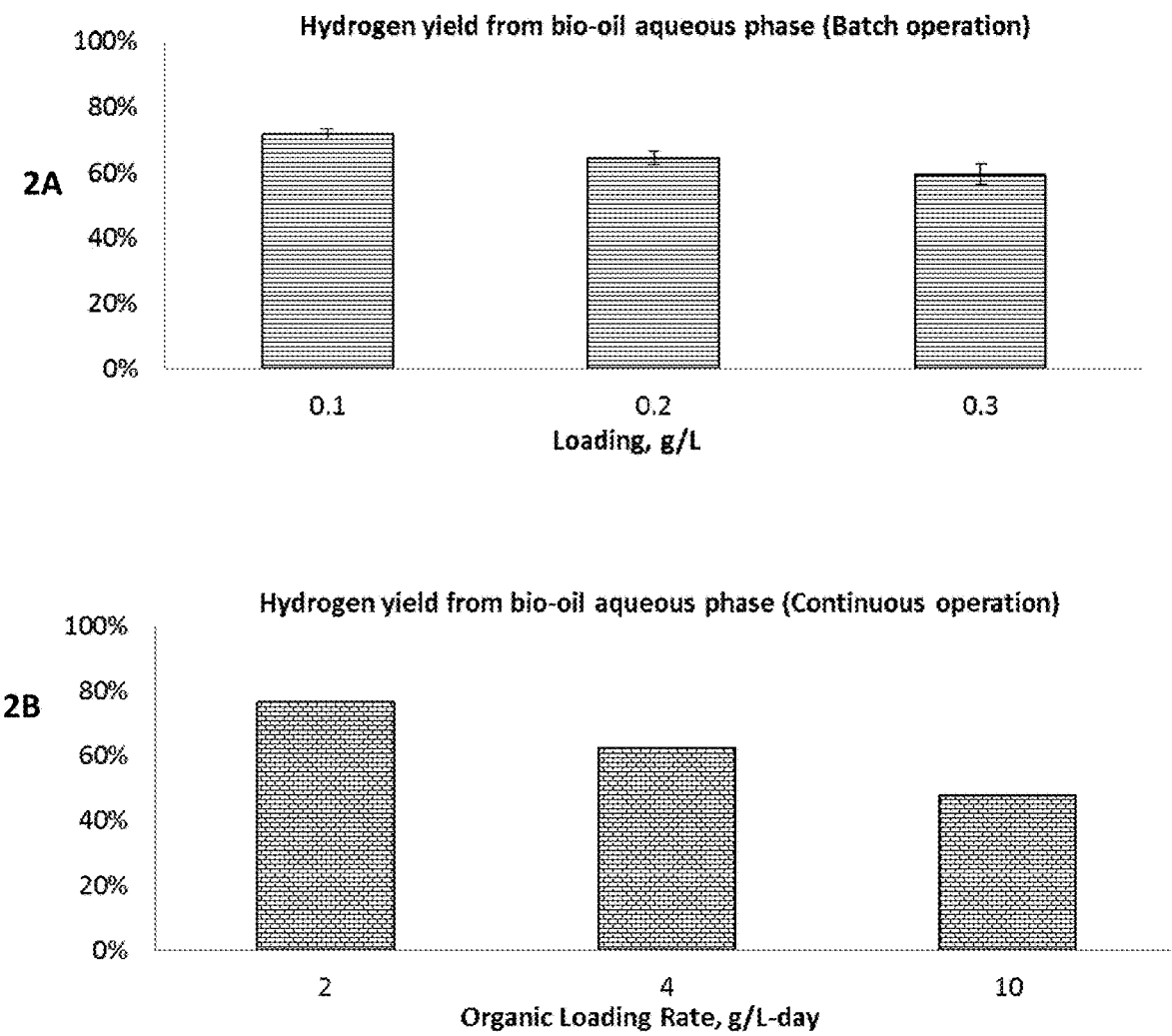
FIGS. 2A, 2B.
Figures 3A, 3B:
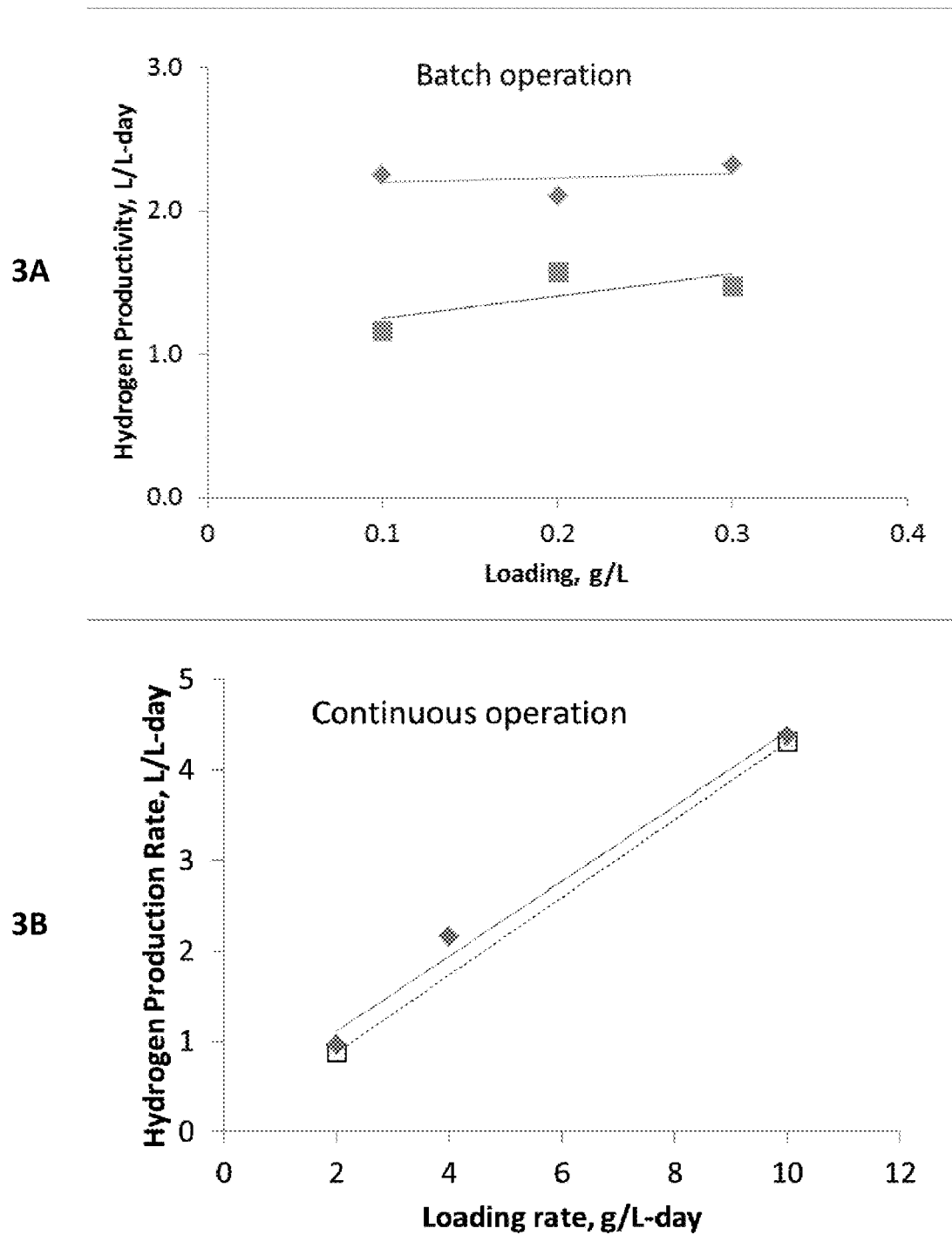
FIGS. 3A, 3B.
Figures 4A, 4B:
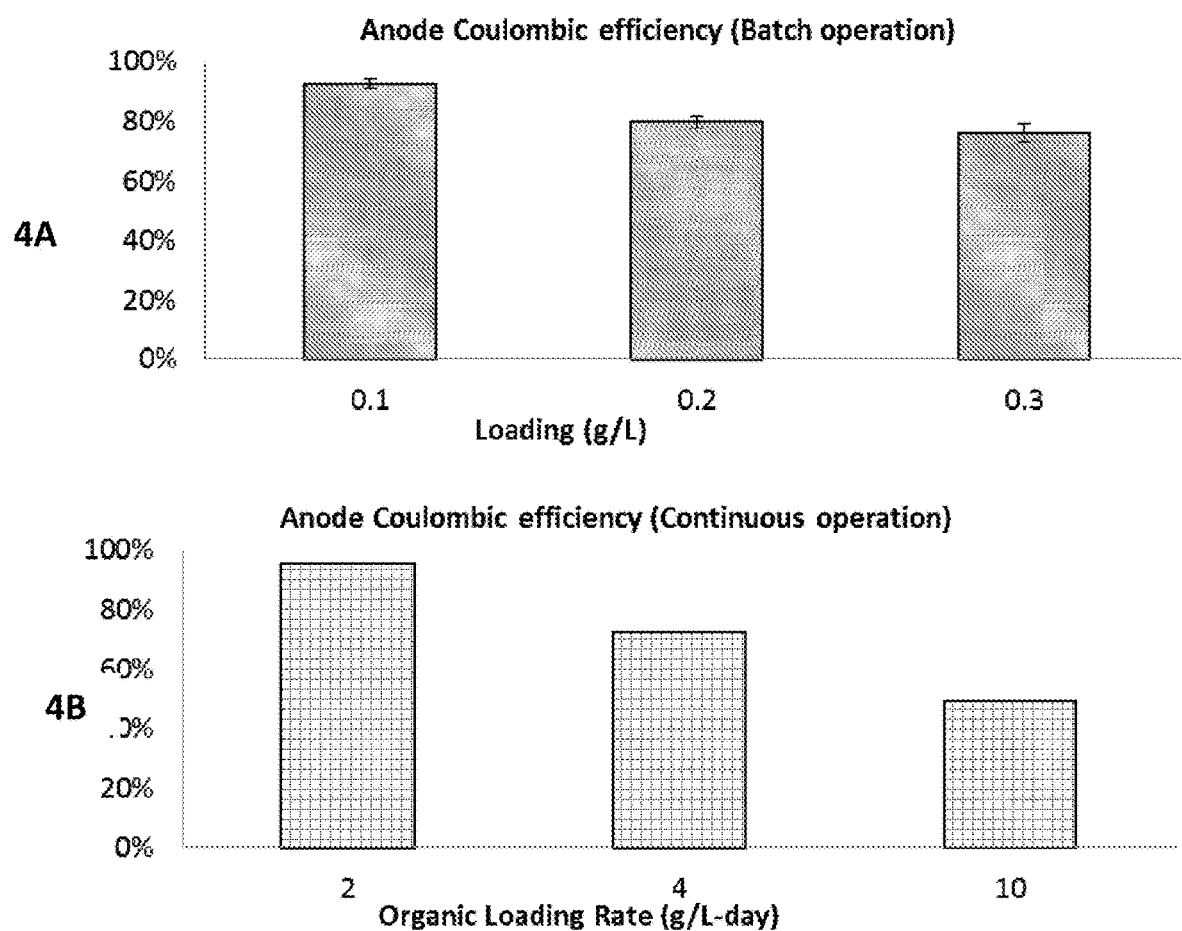
FIGS. 4A, 4B.
Figures 5A, 5B:
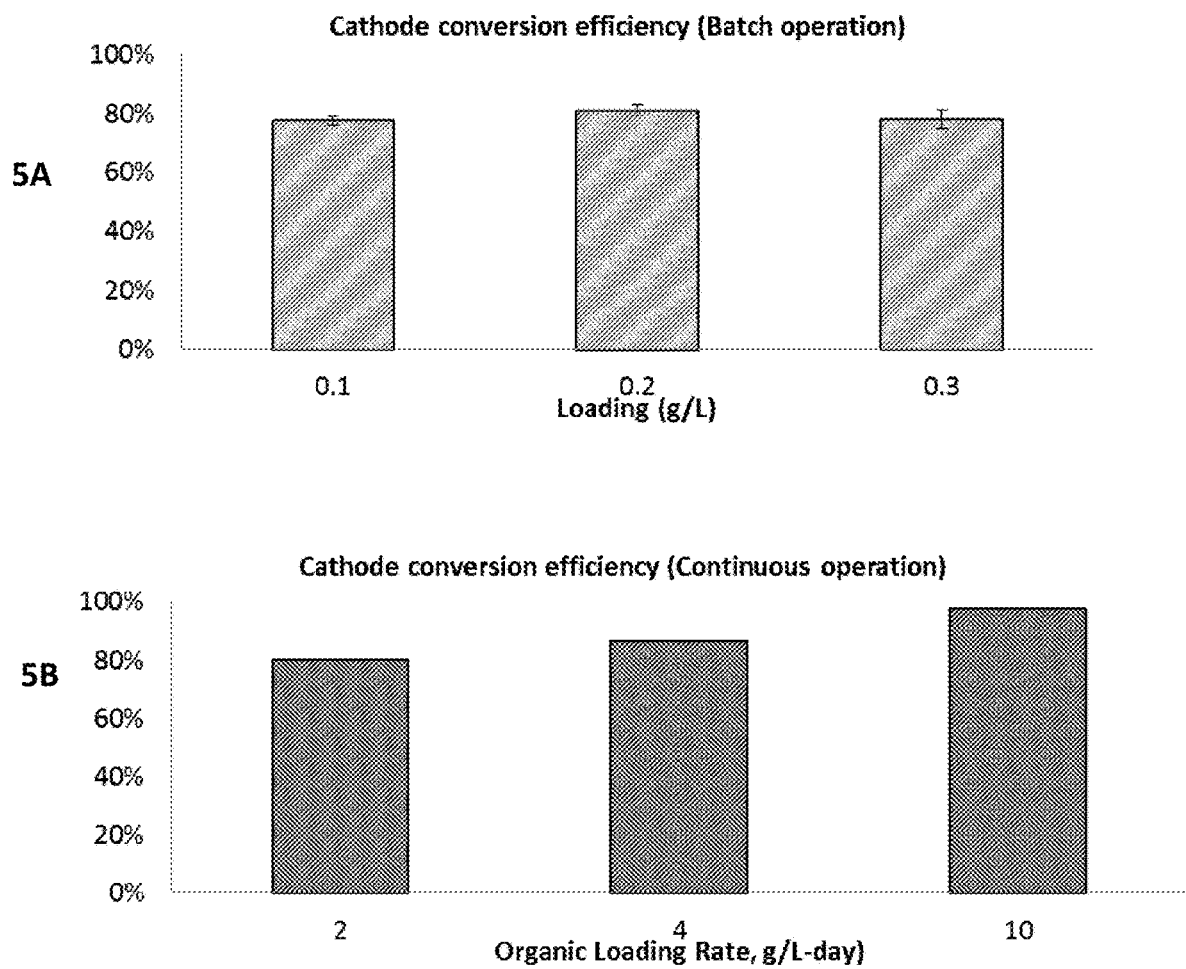
FIGS. 5A, 5B.
Figure 6A:
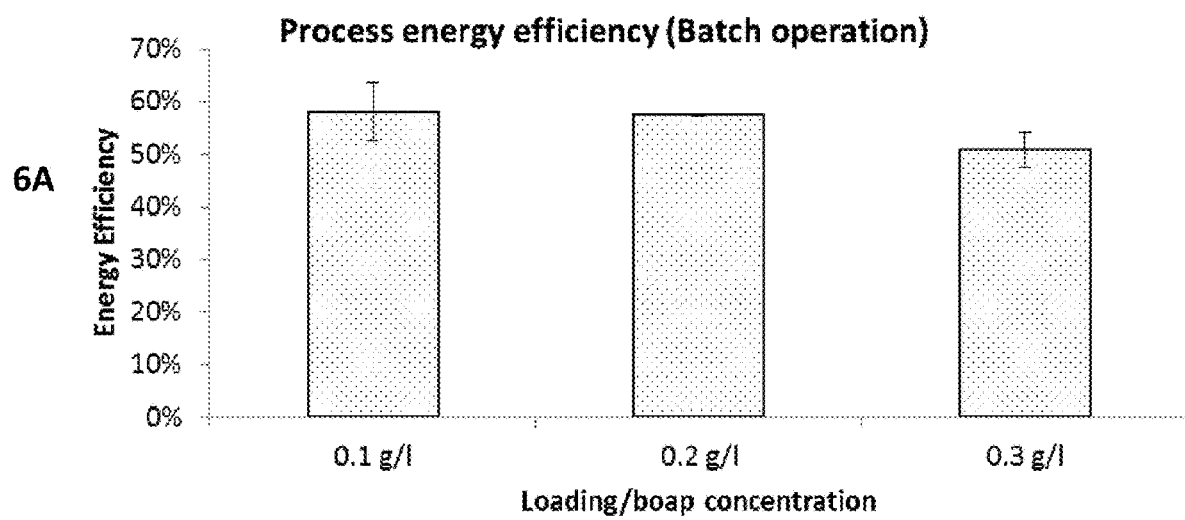
FIGS. 6A, 6B.
Figure 6B:
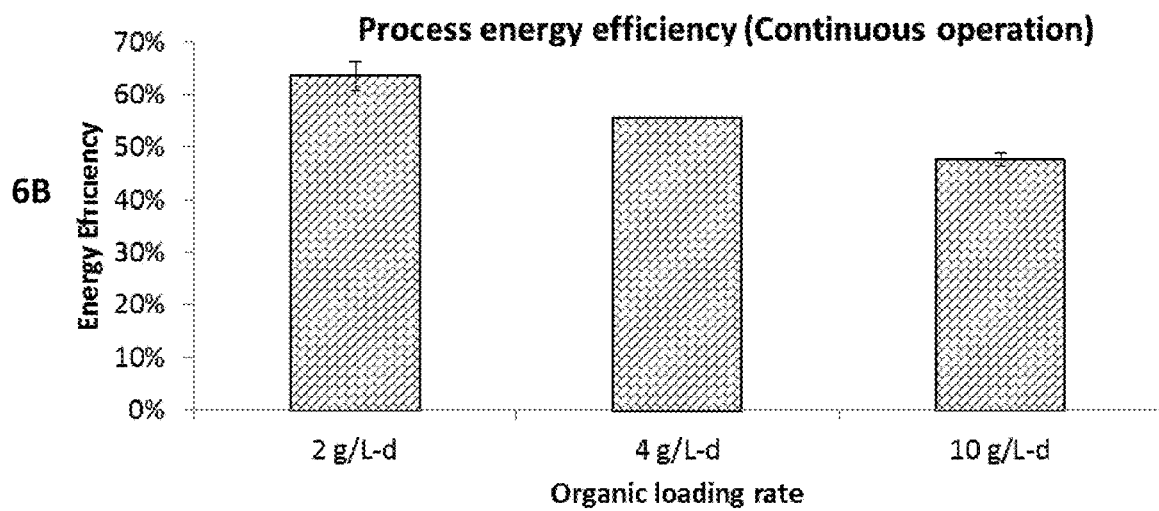
Figures 7A, 7B:
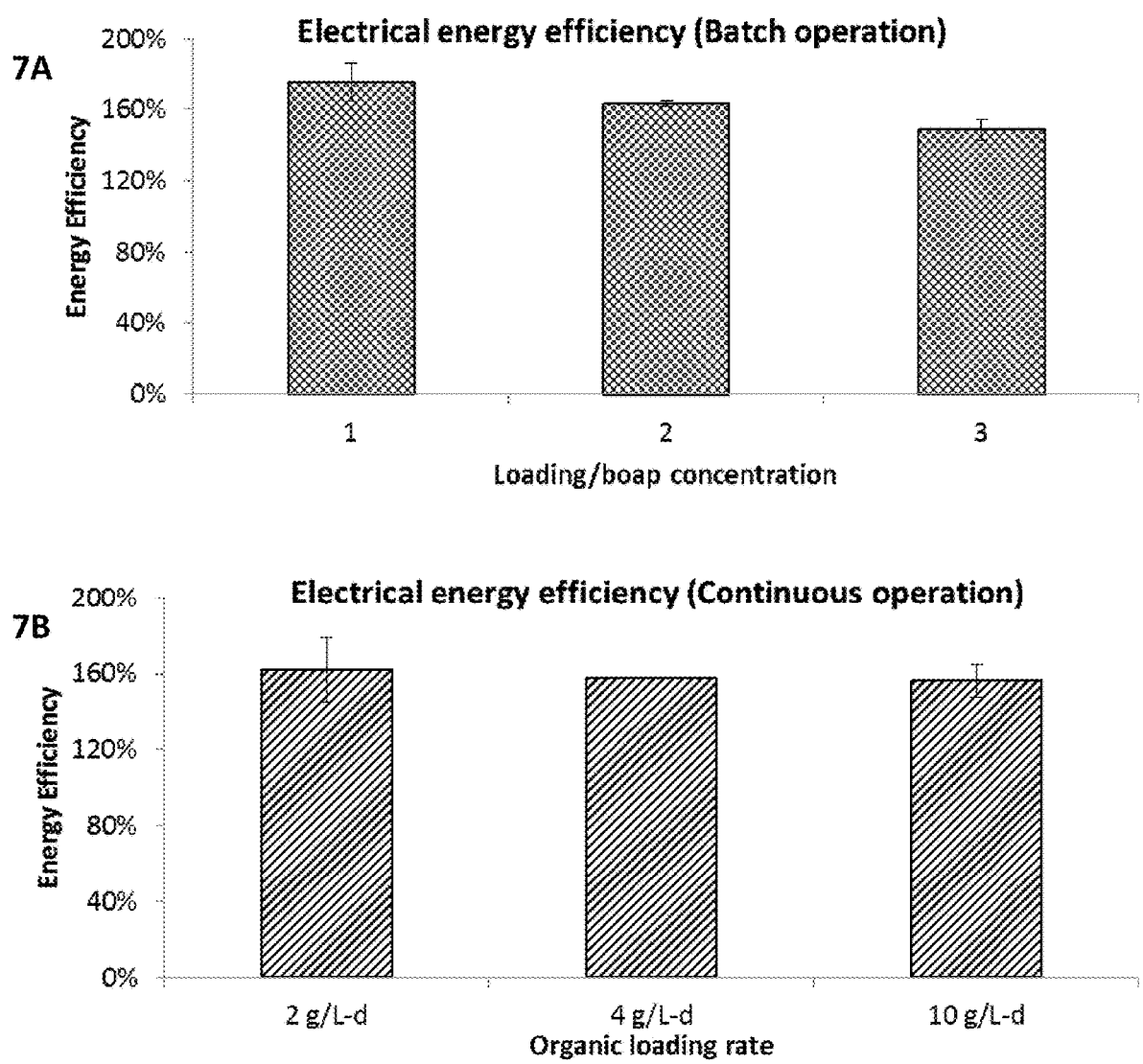
FIGS. 7A, 7B.

FIGS. 2A and 2B (for batch and continuous modes, respectively) show the yield of hydrogen from switchgrass boap. FIGS. 3A, 3B (for batch and continuous modes, respectively) show the productivity of hydrogen in (L $H_2$)/ (L-anode volume per day). The PME process enables high efficiency of conversion of the organics in boap to hydrogen. FIGS. 4A and 4B (for batch and continuous modes, respectively) show the anode coulombic efficiency of hydrogen production, while FIGS. 5A and 5B (for batch and continuous modes, respectively) show the cathode conversion efficiency of the MEC process. All of this results in the high productivity of hydrogen production, as shown in FIGS. 3A and 3B. The efficiency of producing hydrogen from bio-oil aqueous phase is shown in FIGS. 6A and 6B (for batch and continuous modes, respectively). In particular, the electrical energy efficiency for the MEC process is shown in FIGS. 7A and 7B (for batch and continuous modes, respectively), which shows the energy generated in the form of hydrogen is about 50-70% higher than the electrical energy input. This is possible due to use of bio-oil aqueous phase as the chemical energy input into the MEC.

Figure 8A:
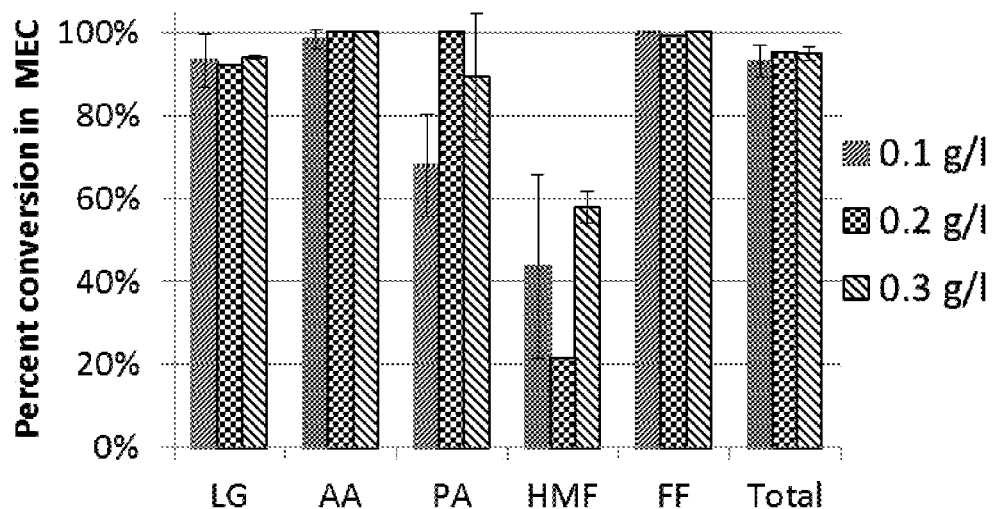
FIGS. 8A, 8B.
Figure 8B:
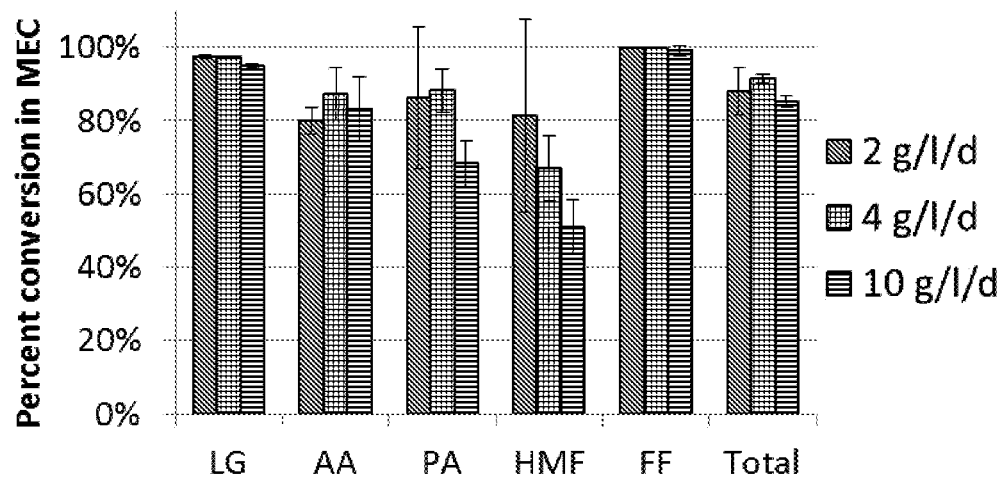
Figure 9A:
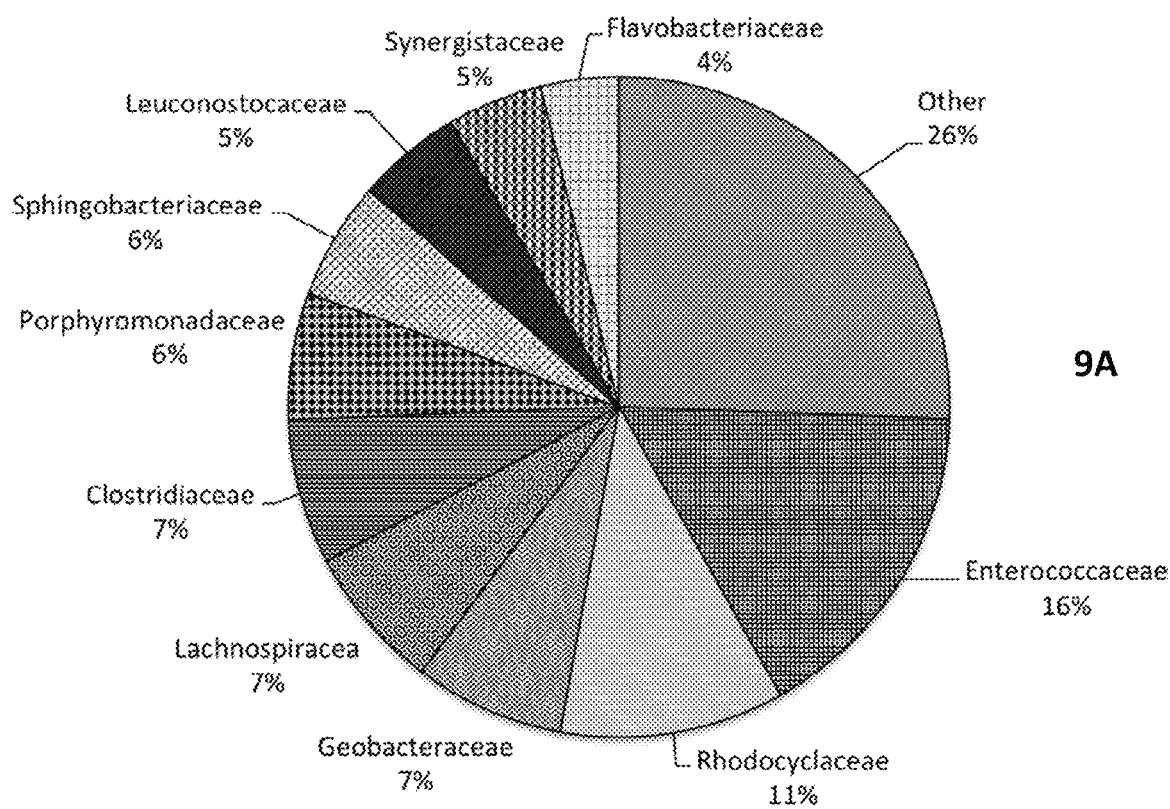
FIGS. 9A, 9B. Pie chart showing anode biofilm composition used for conversion of switchgrass bio-oil aqueous phase in two duplicate MECs.
Figure 9B:
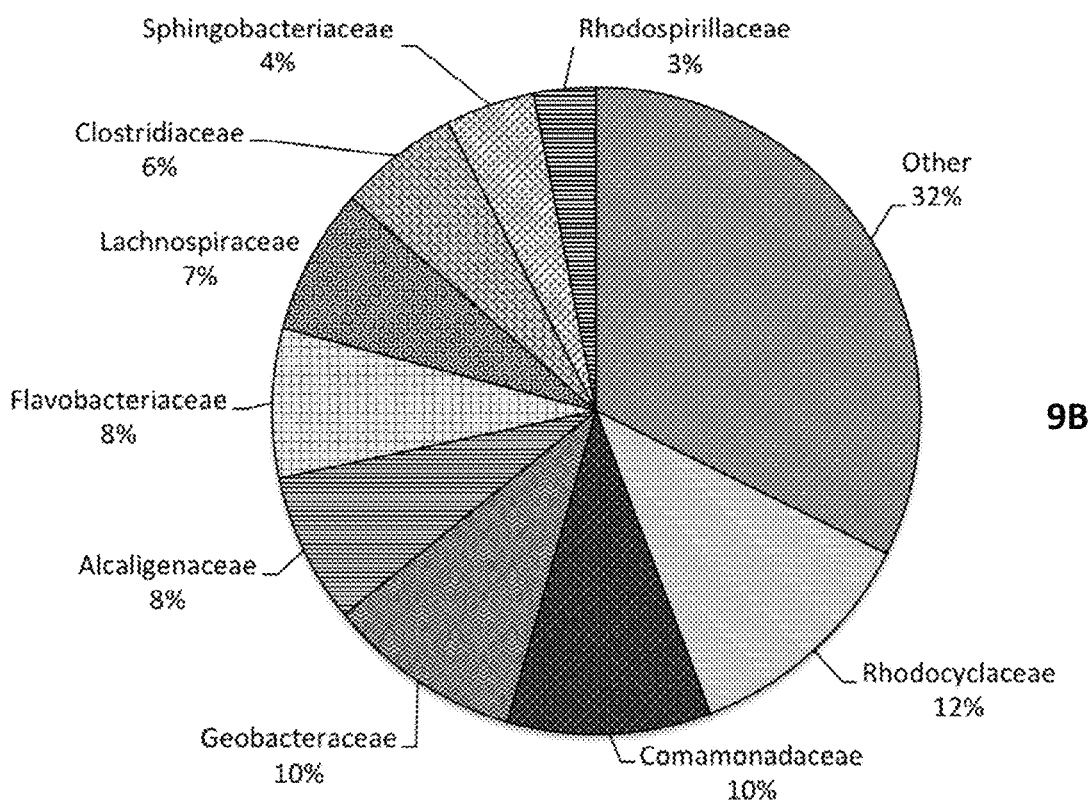
Figure 10A:
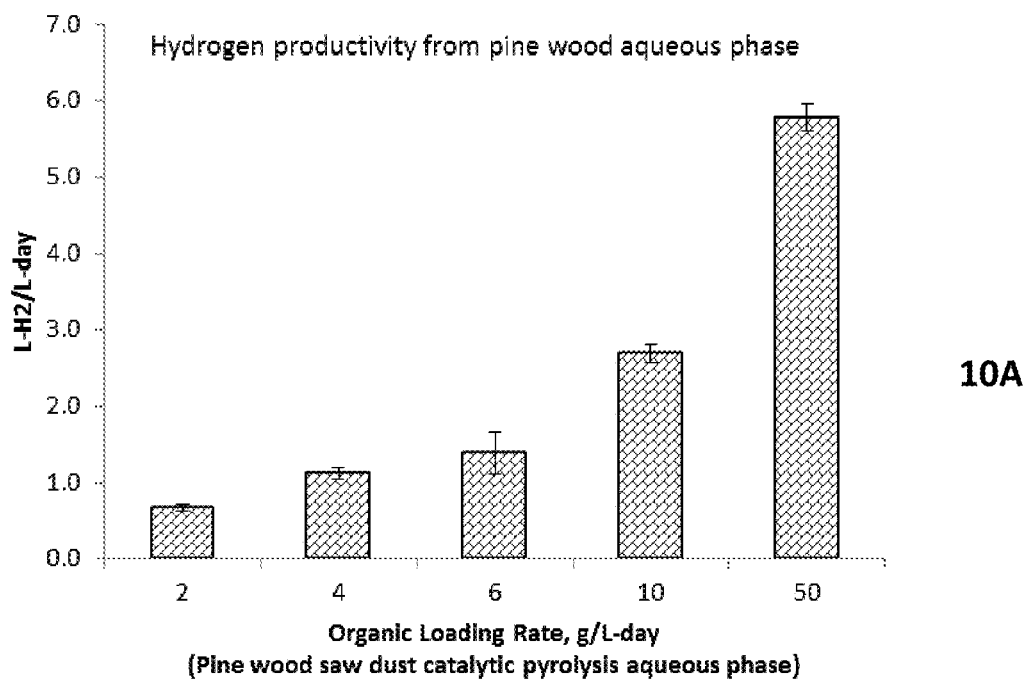
FIGS. 10A, 10B.
Figure 10B:
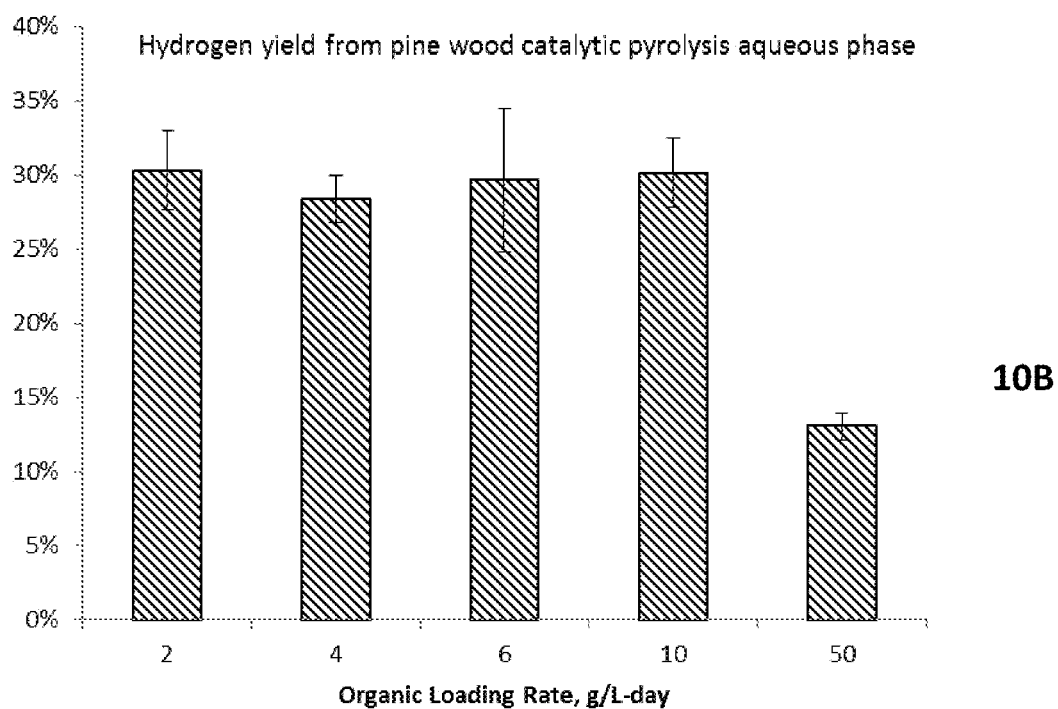
Figure 11:
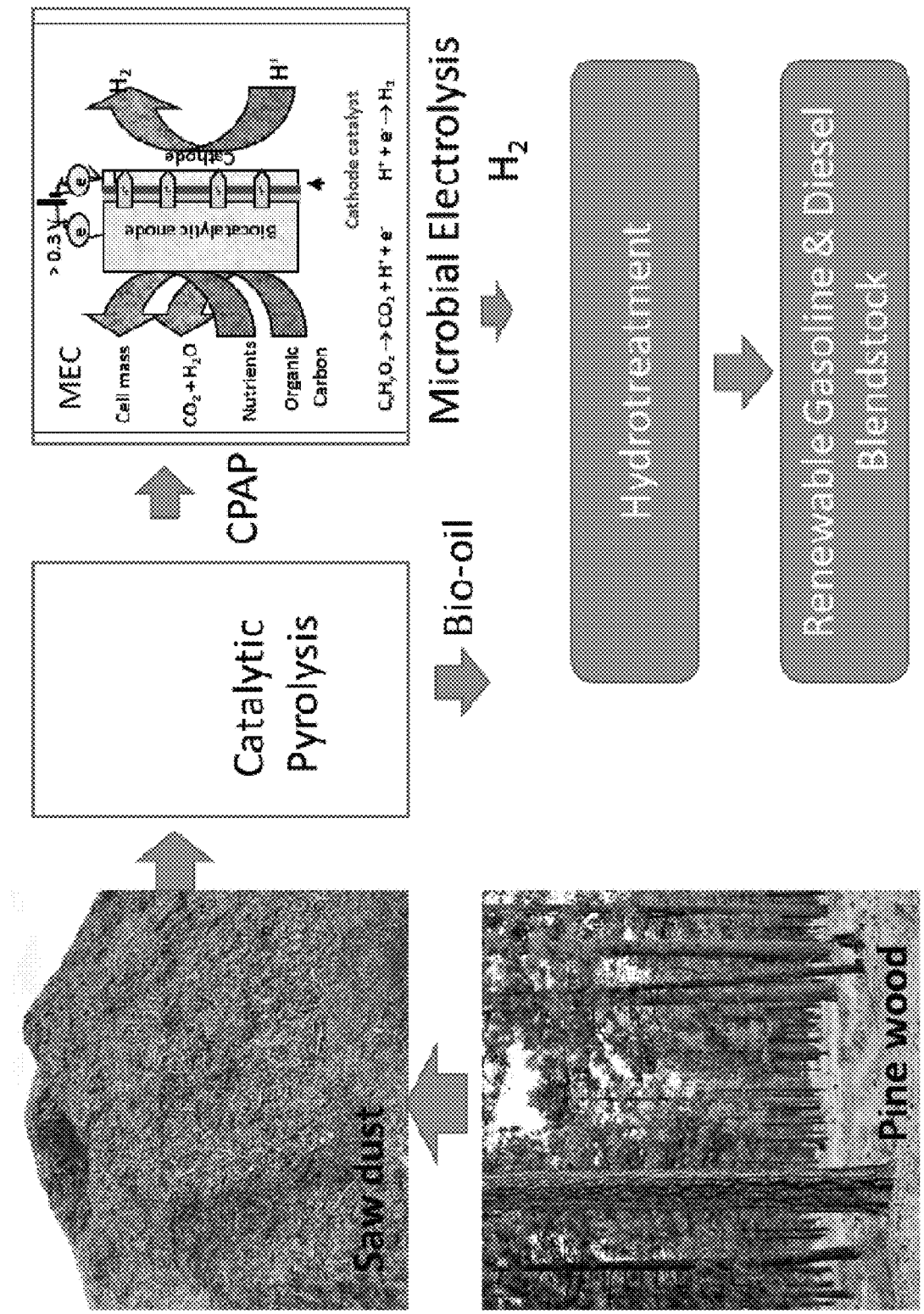
FIG. 11. Schematic showing the overall process of conversion of pine wood to fuels using hydrogen derived from an MEC-pyrolysis integrated process, wherein "CPAP" refers to the aqueous phase.
Figure 12:
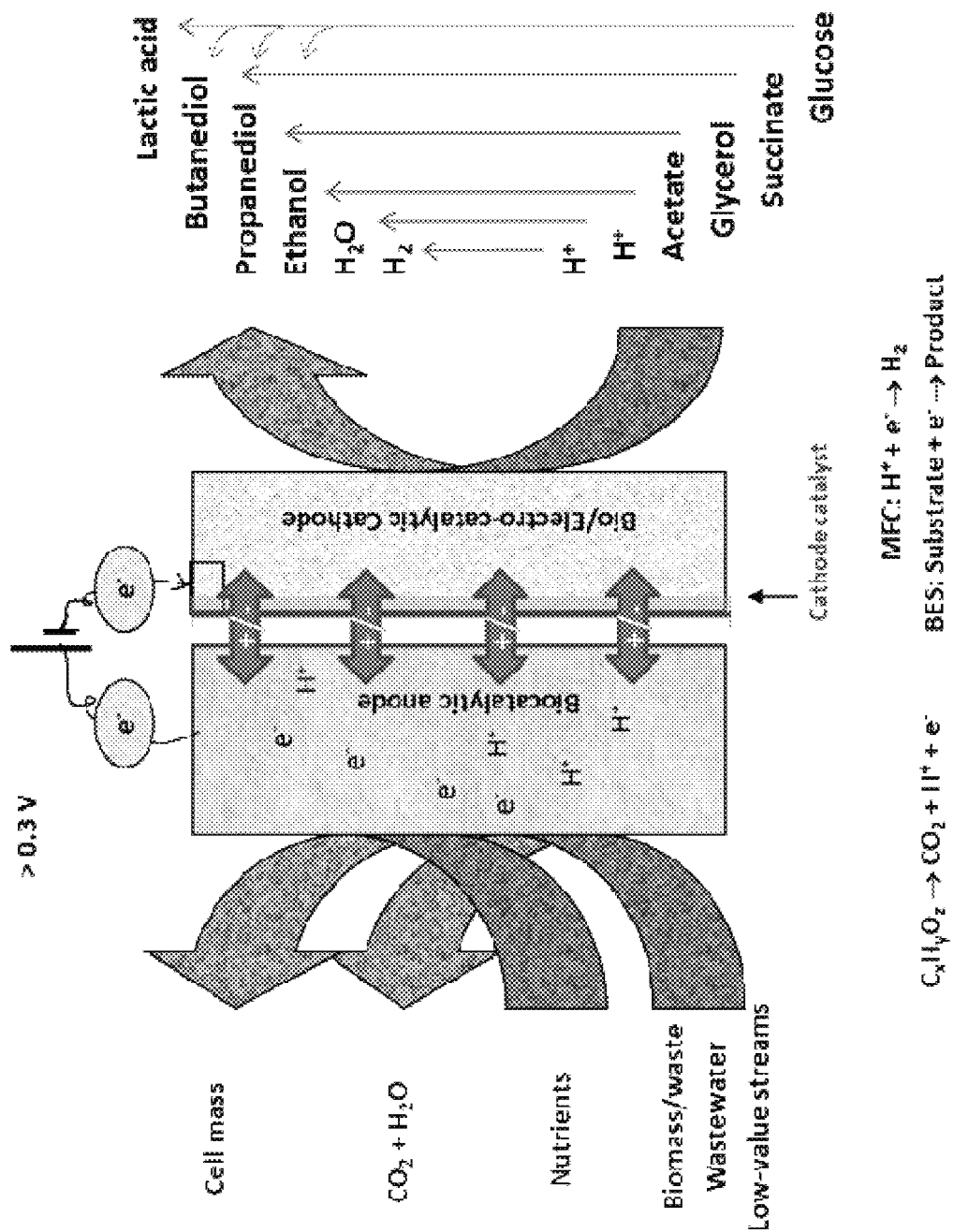
FIG. 12. A schematic diagram of a bioelectrochemical biorefining process converting biomass-derived hydrogenous compounds to electrons at the anode and use of those electrons for producing higher value products at the cathode.

The anode used in the MEC is capable of using a broad range of compounds, such as those found in the biomass-derived aqueous phase. This results in conversion of a range of compounds present in the aqueous phase, as demonstrated by the data provided in FIGS. 8A and 8B (for batch and continuous modes, respectively). The composition of the anode biofilm microbial consortium is shown in FIGS. 9A and 9B. This was determined using 16s rRNA-based genetic characterization of the microbial community. The broad substrate specificity of the anode biofilm is further indicated by its use for conversion of aqueous phase derived from catalytic pyrolysis of pine wood saw dust. FIG. 10A is a graph showing the hydrogen productivity under continuous operation conditions. FIG. 10B is a graph showing the hydrogen yield from pine wood catalytic pyrolysis aqueous phase at organic loading rates from 2 to 50 g/L-day. FIG. 11 shows the overall process of conversion of pine wood to higher value products via use of hydrogen generated in an MEC from the aqueous phase. As shown in the schematic provided in FIG. 12, the electrons derived from the hydrogenous compounds present in aqueous phase can also be used to produce other higher value products, such as alcohols and diols.

Hydrogen is a key reagent in many biorefinery processes as well as a fuel by itself. Since hydrogen is used in many industries, its production by renewable means, as herein described, will favorably impact all such industries. Some of these industries include the production of gasoline and diesel fuel, hydrogenation of plant oils to produce saturated oil, deoxygenation of bio-oil for production of hydrocarbons, production of numerous commodity chemicals, such as monomers for polymers, petrochemical intermediates, fine chemicals, and feedstocks for a range of consumer products.

In the production of liquid fuels from biomass via pyrolysis, the described process has a unique advantage of removing the acidic and corrosive compounds present in bio-oil and extraction of the energy content of those compounds in the form of hydrogen. Thus, use of such unwanted compounds in the production of higher value products represents a significant advance in the art. Moreover, as the unwanted compounds are removed, the resulting bio-oil becomes improved in stability and in its compositional suitability for downstream utilization as a fuel or for production of transportation fuels. The hybrid PME process also leads to significant reduction in life cycle greenhouse gas (GHG) emissions for production of hydrogen by relying on low value hydrogenous materials, such as biomass, as a precursor from which hydrogen and/or other valuable product is obtained. This can also reduce GHG emissions for biomass to fuel production processes by eliminating the need for natural gas and enabling the products to meet the goals of the Renewable Fuels Standard 2. Relative to current technologies for the production of hydrogen from biomass (e.g., autothermal process, combined dark fermentation and photofermentation, steam reforming of biomass, anaerobic digestion-partial oxidation process), the deconstruction-MEC process described herein has unique advantages, including low feedstock costs, high yield, and high productivity.

While there have been shown and described what are at present considered the preferred embodiments of the invention, those skilled in the art may make various changes and modifications which remain within the scope of the invention defined by the appended claims.

What is claimed is:

1. A method for the substantially complete conversion of hydrogenous matter to higher value product, the method comprising:
   (i) subjecting the hydrogenous matter to a substantially complete deconstruction process in which a multiplicity of deconstructed compounds are produced, wherein at least a portion of said deconstructed compounds are oxygenated organic compounds substantially dissolved within an aqueous phase and wherein said deconstruction process is a pyrolysis process; and
   (ii) contacting said aqueous phase with an anode of a microbial electrolysis cell, said anode containing a community of microbes thereon which oxidatively degrade one or more of the oxygenated organic compounds in the aqueous phase to produce protons and free electrons at the anode, wherein the protons migrate from the anode across an ion-permeable partition to a cathode also in the microbial electrolysis cell, wherein the ion-permeable partition separates the anode from the cathode; and the free electrons are transported from the anode to the cathode by an electrically conductive wire connecting the anode with the cathode, and the cell potential of the microbial electrolysis cell is adjusted by application of an external voltage between the anode and the cathode to result in production of said higher value product at the cathode.

2. The method of claim 1, wherein said microbes are in the form of a biofilm on said anode.

3. The method of claim 1, wherein said cathode is constructed of a material capable of reducing protons to hydrogen gas, and wherein hydrogen gas is produced at the cathode.

4. The method of claim 1, wherein said oxygenated organic compounds are selected from the group consisting of organic acid, alcohol, phenol, furan, aldehyde, sugar, ketone compounds, and their oligomers.

5. The method of claim 1, wherein said anode comprises elemental carbon.

6. The method of claim 5, wherein said elemental carbon is a hydrophilized form of carbon.

7. The method of claim 1, wherein said cathode is operated in the substantial absence of oxygen.

8. The method of claim 1, wherein said cathode possesses a surface containing a community of electrotrophic microbes capable of protonation-reduction, wherein at least one organic precursor compound is converted to a reduced organic product at the cathode, and wherein said reduced organic product corresponds to said higher value product.

9. The method of claim 8, wherein the ion-permeable partition is an ion exchange membrane.

10. The method of claim 8, wherein said organic precursor compound is selected from acetate, glycerol, and succinate.

11. The method of claim 8, wherein said reduced organic product is an alcohol or diol.

12. The method of claim 11, wherein said reduced organic product is at least one compound selected from the group consisting of ethanol, butanol, propanediol, and butanediol.

13. The method of claim 1, wherein said aqueous phase is separated from a liquid organic phase also produced in the deconstruction process, and said liquid organic phase is also converted to higher value product.

14. The method of claim 1, wherein said hydrogenous matter is selected from the group consisting of biomass, municipal waste, food waste, and organic industrial waste.

15. The method of claim 1, wherein said microbes at the anode are selected from the group consisting of Proteobacteria and Firmicutes.

16. The method of claim 1, wherein said microbes at the anode are selected from Geobacteraceae, Rhodocyclaceae, Enterococcaceae, and Comamonadaceae.

17. The method of claim 1, wherein said microbes at the anode are initially enriched by feeding the microbes a simulated aqueous phase containing one or more oxygenated compounds actually found in the aqueous phase emanating from said deconstruction process for a period of at least two days before contacting said anode with said aqueous phase emanating from said deconstruction process.

18. A method for the substantially complete conversion of hydrogenous matter to higher value product, the method comprising:
   (i) subjecting hydrogenous matter to a pyrolysis process to produce a crude pyrolysis oil comprising an organic phase rich in hydrocarbons substantially insoluble in water and an aqueous phase rich in oxygenated organic compounds soluble in water, wherein said pyrolysis process results in the substantially complete deconstruction of the hydrogenous matter;

(ii) separating said aqueous phase from said organic phase rich in hydrocarbons; and (iii) contacting said aqueous phase with an anode of a microbial electrolysis cell, said anode containing a community of microbes thereon which oxidatively degrade one or more of the oxygenated organic compounds in the aqueous phase to produce protons and free electrons at the anode, wherein the protons migrate from the anode across an ion-permeable partition to a cathode also in the microbial electrolysis cell, wherein the ion-permeable partition separates the anode from the cathode; and the free electrons are transported from the anode to the cathode by an electrically conductive wire connecting the anode with the cathode, and the cell potential of the microbial electrolysis cell is adjusted by application of an external voltage between the anode and the cathode to result in production of the higher value product at the cathode.

19. The method of claim 18, wherein said cathode is constructed of a material capable of reducing protons to hydrogen gas, and wherein hydrogen gas is produced at the cathode.

20. The method of claim 19, wherein said cathode possesses a surface containing a community of electrotrophic microbes capable of protonation-reduction, wherein at least one organic precursor compound is converted to a reduced organic product at the cathode, and wherein said reduced organic product corresponds to said higher value product.

21. The method of claim 20, wherein said organic precursor compound is selected from acetate, glycerol, and succinate.

22. The method of claim 21, wherein said reduced organic product is at least one compound selected from the group consisting of ethanol, butanol, propanediol, and butanediol.

23. The method of claim 20, wherein said reduced organic product is an alcohol or diol.

24. The method of claim 18, wherein the ion-permeable partition is an ion exchange membrane.

* * * * *